(12) United States Patent
Tsuruta

(10) Patent No.: US 10,357,229 B2
(45) Date of Patent: Jul. 23, 2019

(54) ULTRASOUND ENDOSCOPE, SUCTION APPARATUS FOR ULTRASOUND ENDOSCOPE, AND ULTRASOUND ENDOSCOPE SYSTEM

(71) Applicant: OLYMPUS CORPORATION, Tokyo (JP)

(72) Inventor: Teppei Tsuruta, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 233 days.

(21) Appl. No.: 15/341,671

(22) Filed: Nov. 2, 2016

(65) Prior Publication Data

US 2017/0049415 A1 Feb. 23, 2017

Related U.S. Application Data

(63) Continuation of application No. PCT/JP2015/078658, filed on Oct. 8, 2015.

(30) Foreign Application Priority Data

Oct. 28, 2014 (JP) ................. 2014-219676

(51) Int. Cl.
*A61B 8/00* (2006.01)
*A61B 1/00* (2006.01)
(Continued)

(52) U.S. Cl.
CPC ............... *A61B 8/54* (2013.01); *A61B 1/005* (2013.01); *A61B 1/0008* (2013.01);
(Continued)

(58) Field of Classification Search
CPC ... A61B 8/00; A61B 1/00066; A61B 1/00091; A61B 1/00094; A61B 1/00137;
(Continued)

(56) References Cited

U.S. PATENT DOCUMENTS 4,325,362 A * 4/1982 Ouchi ...................... A61B 1/12
600/158
5,265,612 A * 11/1993 Sarvazyan ............. A61B 5/036
600/471
(Continued)

FOREIGN PATENT DOCUMENTS

JP H05-103746 A 4/1993
JP 2001-224594 A 8/2001
(Continued)

OTHER PUBLICATIONS

International Search Report dated Dec. 28, 2015 issued in PCT/JP2015/078658.
(Continued)

*Primary Examiner* — Amanda Lauritzen Moher
(74) *Attorney, Agent, or Firm* — Scully, Scott, Murphy & Presser, P.C.

(57) ABSTRACT

An ultrasound endoscope includes: an ultrasound probe arranged in a distal end rigid portion; a suction and forceps port provided in a vicinity of the ultrasound probe; a treatment instrument insertion channel and a negative pressure channel communicating with the suction and forceps port; and a control valve configured to variably regulate a negative pressure for suction that is transmitted to the suction and forceps port through the treatment instrument insertion channel and the negative pressure channel to two or more states.

9 Claims, 18 Drawing Sheets

(51) Int. Cl.
*A61B 1/005* (2006.01)
*A61B 5/00* (2006.01)
*A61B 1/012* (2006.01)
*A61B 8/12* (2006.01)
*A61B 1/015* (2006.01)
*A61B 8/08* (2006.01)
*A61M 1/00* (2006.01)

(52) U.S. Cl.
CPC ...... *A61B 1/00064* (2013.01); *A61B 1/00066* (2013.01); *A61B 1/00068* (2013.01); *A61B 1/00071* (2013.01); *A61B 1/00091* (2013.01); *A61B 1/00094* (2013.01); *A61B 1/00137* (2013.01); *A61B 1/012* (2013.01); *A61B 1/015* (2013.01); *A61B 5/683* (2013.01); *A61B 5/6834* (2013.01); *A61B 8/12* (2013.01); *A61B 8/4281* (2013.01); *A61B 8/44* (2013.01); *A61B 8/445* (2013.01); *A61B 8/4444* (2013.01); *A61B 8/485* (2013.01); *A61B 8/5207* (2013.01); *A61B 1/00131* (2013.01); *A61B 8/08* (2013.01); *A61M 1/00* (2013.01); *A61M 1/0088* (2013.01)

(58) Field of Classification Search
CPC .. A61B 1/015; A61B 8/08; A61B 8/12; A61B 8/485; A61B 8/5207; A61B 8/54; A61B 1/012; A61B 1/00064; A61B 5/6834; A61B 5/683; A61B 8/4444; A61B 8/445; A61B 8/44; A61B 1/0008; A61B 1/00071; A61B 1/005; A61B 1/00068; A61B 8/4281; A61B 1/00131; A61M 1/0088; A61M 1/00
See application file for complete search history.

(56) References Cited

U.S. PATENT DOCUMENTS

| | | | | |
|---|---|---|---|---|
| 5,524,636 | A * | 6/1996 | Sarvazyan | A61B 1/0052 600/587 |
| 6,626,855 | B1 * | 9/2003 | Weng | A61B 8/12 600/439 |
| 8,241,204 | B2 * | 8/2012 | Spivey | A61B 1/00087 600/104 |
| 8,781,275 | B2 * | 7/2014 | Asselin | A61B 18/22 385/39 |
| 9,332,964 | B2 * | 5/2016 | Miyake | A61B 8/5207 |
| 2004/0073106 | A1 * | 4/2004 | Lee | A61B 90/17 600/415 |
| 2008/0269606 | A1 * | 10/2008 | Matsumura | A61B 5/0048 600/438 |
| 2008/0300460 | A1 | 12/2008 | Sugita | |
| 2009/0281429 | A1 | 11/2009 | Nishina et al. | |
| 2010/0114325 | A1 * | 5/2010 | Yang | A61F 2/04 623/23.7 |
| 2012/0209119 | A1 * | 8/2012 | Ohshima | A61B 8/4477 600/443 |
| 2013/0046138 | A1 * | 2/2013 | McLawhorn | A61B 1/00087 600/104 |
| 2013/0066267 | A1 * | 3/2013 | Kwok | A61F 5/0089 604/99.01 |
| 2013/0104884 | A1 * | 5/2013 | Vazales | A61B 1/267 128/202.16 |
| 2013/0110109 | A1 * | 5/2013 | Nguyen | A61B 17/32056 606/46 |
| 2013/0296847 | A1 * | 11/2013 | Germain | A61B 18/1206 606/39 |
| 2014/0276547 | A1 * | 9/2014 | Lonky | A61M 1/0066 604/503 |
| 2016/0157703 | A1 * | 6/2016 | Brooks | A61B 1/00094 600/104 |
| 2016/0183800 | A1 * | 6/2016 | Schaffer | A61B 17/3203 606/130 |
| 2017/0055942 | A1 * | 3/2017 | Tsuruta | A61B 8/12 |

FOREIGN PATENT DOCUMENTS

| | | |
|---|---|---|
| JP | 2008-289761 A | 12/2008 |
| JP | 2009-268751 A | 11/2009 |
| JP | 2012-081295 A | 4/2012 |

OTHER PUBLICATIONS

Yassine Mofid et al, "In-vivo imaging of skin under stress: potential of high-frequency (20 MHz) static 2-d elastography", IEEE Transactions on Ultrasonics, Ferroelectrics, and Frequency Control, May 2006, pp. 925-935, vol. 53 No. 5.

* cited by examiner

ULTRASOUND ENDOSCOPE, SUCTION APPARATUS FOR ULTRASOUND ENDOSCOPE, AND ULTRASOUND ENDOSCOPE SYSTEM

CROSS REFERENCE TO RELATED APPLICATION

This application is a continuation application of PCT/JP2015/078658 filed on Oct. 8, 2015 and claims benefit of Japanese Application No. 2014-219676 filed in Japan on Oct. 28, 2014, the entire contents of which are incorporated herein by this reference.

BACKGROUND OF THE INVENTION

1. Field of the Invention

The present invention relates to an ultrasound endoscope equipped with an ultrasound probe at a distal end of an insertion portion, a suction apparatus for an ultrasound endoscope that is compatible with the ultrasound endoscope, and an ultrasound endoscope system.

2. Description of the Related Art

In recent years, elastography that displays the hardness of living tissue has been practically applied to ultrasound observation that uses an ultrasound diagnostic apparatus (for example, see Japanese Patent Application Laid-Open Publication No. 2012-81295). According to elastography technology, for example, a change (displacement) in a deformed state of living tissue is measured by changing a pressing state of an ultrasound probe with respect to an organ that can be detected using ultrasound to two or more states, and an elastographic image can be constructed based on a deformation (strain) obtained by spatially differentiating such displacement.

It is anticipated that such elastography technology will be applied to various kinds of ultrasound observation apparatuses, and that, for example, the detection rate for lesions in deep organs can be improved by applying elastography technology to an ultrasound endoscope having an ultrasound probe at a distal end of an insertion portion.

SUMMARY OF THE INVENTION

An ultrasound endoscope according to one aspect of the present invention includes: an insertion portion that is long and has flexibility and is to be inserted into a subject; a distal end portion that is disposed at a distal end of the insertion portion; an ultrasound observation portion that is arranged in the distal end portion; a suction port that is provided in a vicinity of the ultrasound observation portion; a fluid conduit communicating with the suction port; and a first negative pressure regulation portion configured to periodically change a negative pressure for suction that is transmitted to the suction port through the fluid conduit, by controlling the negative pressure for suction at an arbitrary duty ratio.

Further, a suction apparatus for an ultrasound endoscope according to one aspect of the present invention is a suction apparatus that is compatible with an ultrasound endoscope including an insertion portion that is long and has flexibility and is to be inserted into a subject, a distal end portion that is disposed at a distal end of the insertion portion, an ultrasound observation portion that is arranged in the distal end portion, a suction port that is provided in a vicinity of the ultrasound observation portion, and a fluid conduit communicating with the suction port; the suction apparatus including: a negative pressure generation portion configured to generate a negative pressure for suction that is transmitted to the suction port; and a second negative pressure regulation portion configured to periodically change a negative pressure for suction that is transmitted from the negative pressure generation portion to the suction port through the fluid conduit by controlling the negative pressure for suction at an arbitrary duty ratio.

An ultrasound endoscope system according to one aspect of the present invention includes: the ultrasound endoscope; a pressing control portion configured to control a pressing state in which the ultrasound observation portion presses the subject, by controlling a negative pressure for suction that is transmitted to the suction port by means of negative pressure regulation through the first negative pressure regulation portion; a probe control portion configured to perform driving control of the ultrasound observation portion in two or more pressing states that are controlled by the pressing control portion, and acquire an ultrasound signal with respect to the subject; and an elasticity image generation portion configured to measure a displacement amount of the subject based on the ultrasound signal, and generate an elasticity image that shows a distribution of an elasticity modulus for each coordinate of the subject based on the displacement amount.

Further, an ultrasound endoscope system according to another aspect of the present invention is equipped with: the suction apparatus for an ultrasound endoscope; a pressing control portion configured to control a pressing state in which the ultrasound observation portion presses the subject, by controlling a negative pressure for suction that is transmitted to the suction port by means of negative pressure regulation through the second negative pressure regulation portion; a probe control portion configured to perform driving control of the ultrasound observation portion in two or more pressing states that are controlled by the pressing control portion, and acquire an ultrasound signal with respect to the subject; and an elasticity image generation portion configured to measure a displacement amount of the subject based on the ultrasound signal, and generate an elasticity image that shows a distribution of an elasticity modulus for each coordinate of the subject based on the displacement amount.

DETAILED DESCRIPTION OF THE PREFERRED EMBODIMENTS

Figure 1:
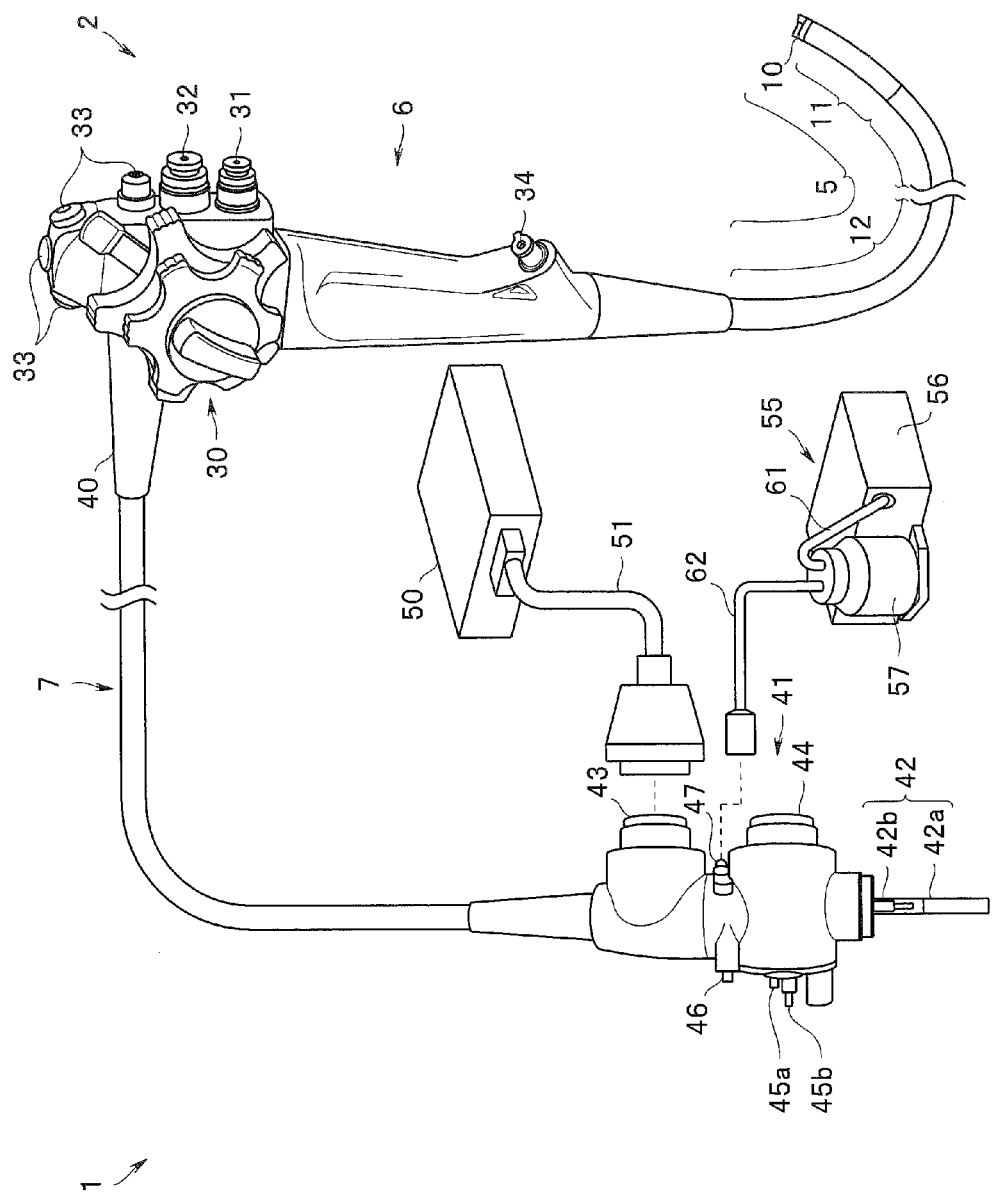
FIG. 1 is a configuration diagram of an ultrasound endoscope system according to a first embodiment of the present invention.
Figure 2:
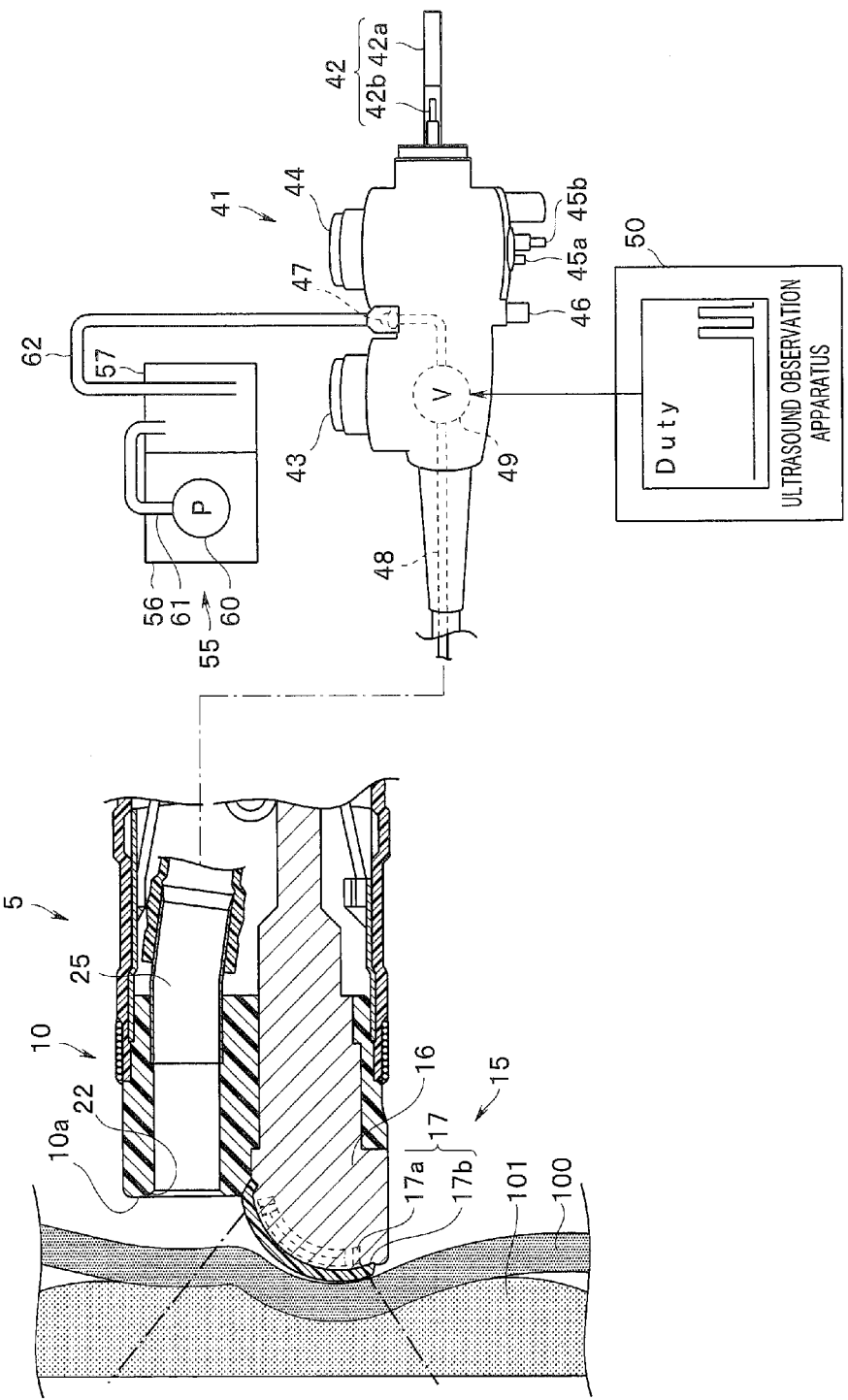
FIG. 2 is an explanatory drawing that schematically illustrates a relation between an ultrasound probe and a gastric wall when suction is not performed according to the first embodiment of the present invention.
Figure 3:
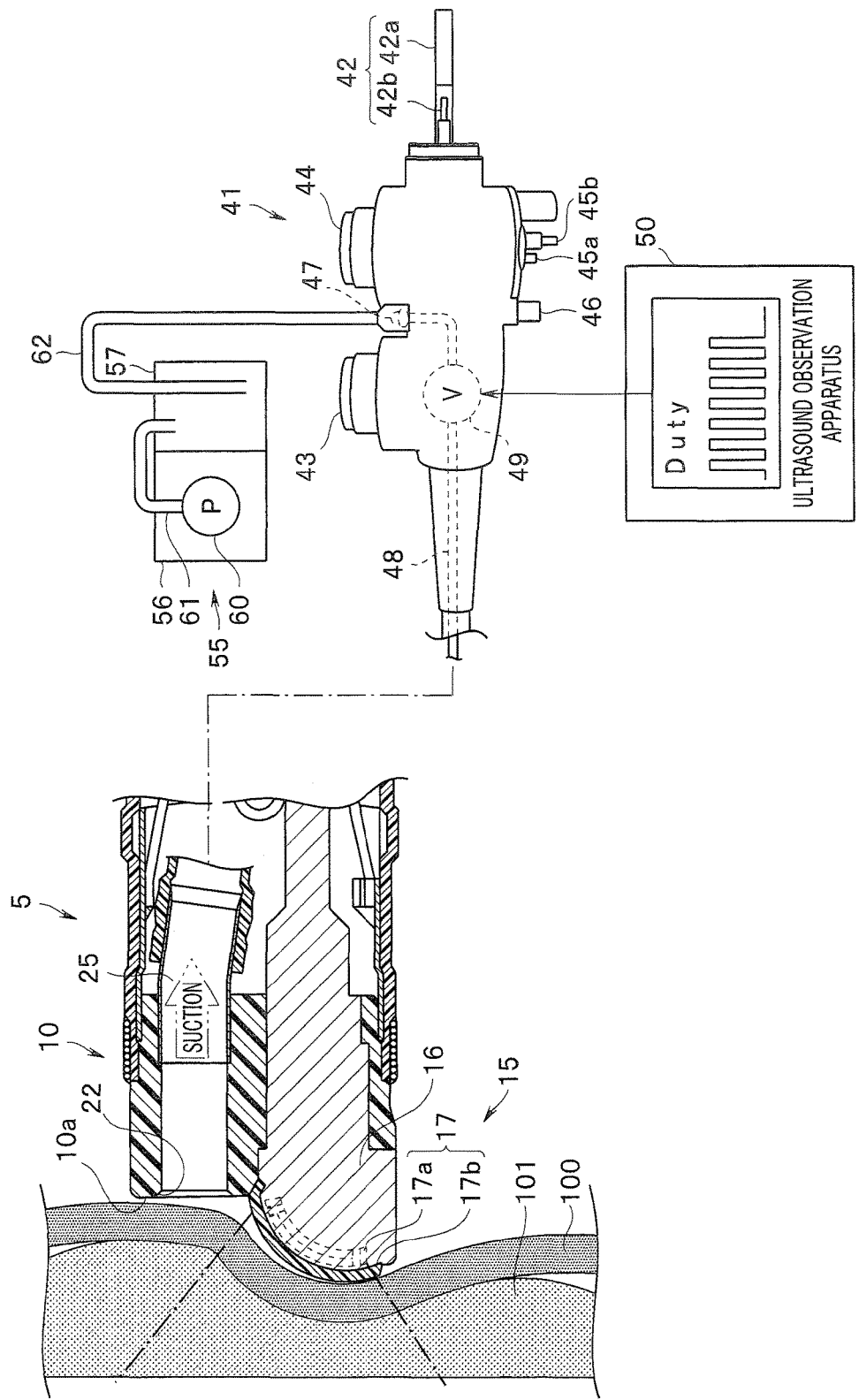
FIG. 3 is an explanatory drawing that schematically illustrates a relation between an ultrasound probe and a gastric wall when suction is performed according to the first embodiment of the present invention.
Figure 4:
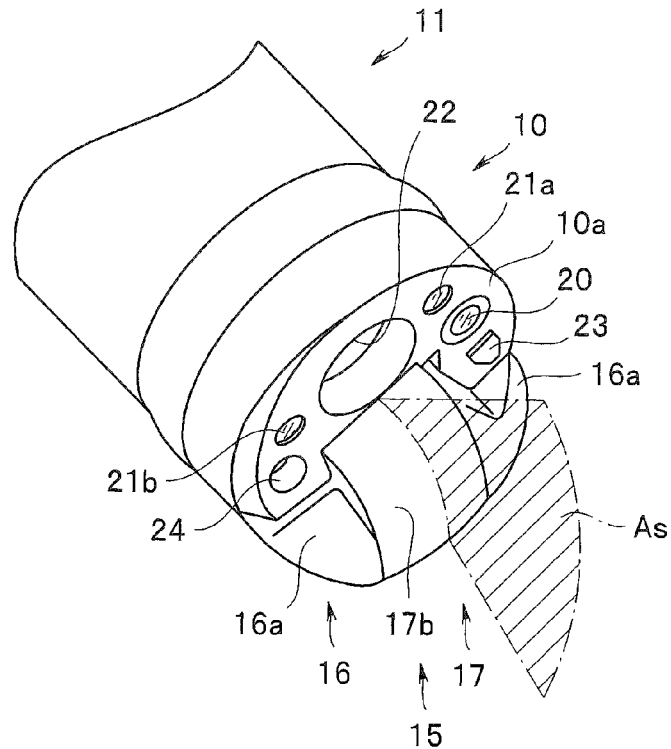
FIG. 4 is a perspective view illustrating a distal end portion according to the first embodiment of the present invention.
Figure 5:
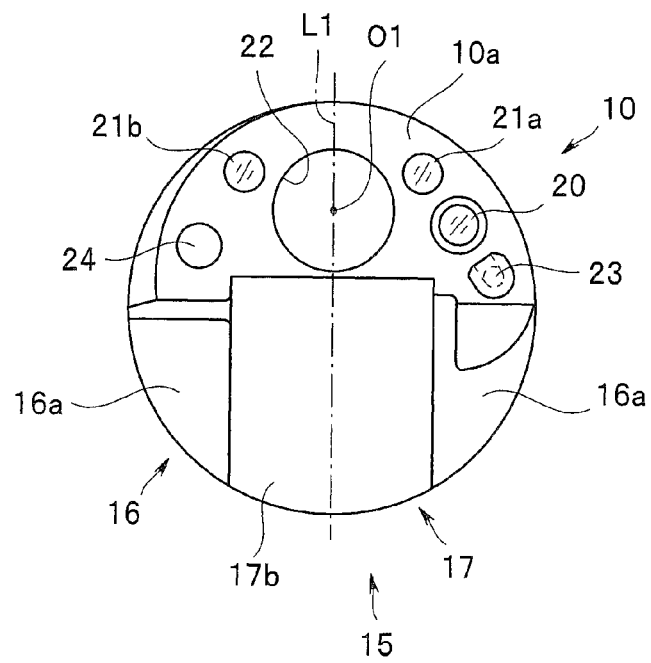
FIG. 5 is an end view illustrating the distal end portion according to the first embodiment of the present invention.

Embodiments of the present invention will be described hereunder with reference to the accompanying drawings. FIGS. 1 to 5 relate to one embodiment of the present invention, of which FIG. 1 is a configuration diagram of an ultrasound endoscope system, FIG. 2 is an explanatory drawing that schematically illustrates a relation between an ultrasound probe and a gastric wall when suction is not performed, FIG. 3 is an explanatory drawing that schematically illustrates a relation between the ultrasound probe and the gastric wall when suction is performed, FIG. 4 is a perspective view illustrating a distal end portion, and FIG. 5 is an end view illustrating the distal end portion.

An ultrasound endoscope system 1 of the present embodiment that is shown in FIG. 1 has, for example, an ultrasound endoscope for use in the stomach and duodenum (hereunder, also referred to as simply "endoscope") 2. The endoscope 2 includes an elongated insertion portion 5 that is to be inserted into a body cavity, an operation portion 6 that is provided at a proximal end of the insertion portion 5, and a universal cord 7 that extends from the operation portion 6.

The insertion portion 5 includes a distal end rigid portion 10, a bending portion 11 that is positioned at a proximal end of the distal end rigid portion 10, and a flexible tube portion 12 having flexibility that is thin and long and which is positioned at a proximal end of the bending portion 11 and runs to the operation portion 6, and these portions are provided in this order from the distal end side in a connected row arrangement to constitute a main part of the insertion portion 5.

As shown in FIG. 2 to FIG. 5, an ultrasound unit 15 for obtaining acoustic image information by ultrasound is provided in the distal end rigid portion 10. The ultrasound unit 15 of the present embodiment is a convex-type ultrasound unit. The ultrasound unit 15 includes a nosepiece 16 that is a housing, and an ultrasound probe 17 as an ultrasound observation portion.

The nosepiece 16 has, for example, a tissue contact face 16a formed in a convex, partial arc shape. The tissue contact face 16a protrudes further to the front than a distal end face 10a of the distal end rigid portion 10 (see FIGS. 4 and 5).

The ultrasound probe 17 has a plurality of ultrasound transducers 17a that are arrayed in a convex, partial arc shape, and an acoustic lens 17b that covers the front of the ultrasound transducers 17a (see FIGS. 2 and 3). The ultrasound probe 17 is arranged at approximately the center of the tissue contact face 16a of the nosepiece 16 (see FIGS. 4 and 5). Further, the acoustic lens 17b of the ultrasound probe 17 is protruded further to the front than the distal end face 10a of the distal end rigid portion 10 together with the tissue contact face 16a of the nosepiece 16, and by this means it is possible for the ultrasound probe 17 to mainly scan living tissue and the like located at the front in the insertion direction of the endoscope.

Further, for example, as shown in FIGS. 4 and 5, an observation window 20 constituting part of an observation optical system, a pair of illuminating windows 21a and 21b constituting part of an illumination optical system, a suction and forceps port 22 as a suction port through which a treatment instrument such as a puncture needle is led out, an air/water feeding nozzle 23 that ejects a fluid such as air or water toward the observation window 20, and an auxiliary water feeding channel port 24 that ejects a fluid such as water toward the front of the distal end rigid portion 10 (that is, in the protruding direction of the ultrasound probe 17) are provided in the distal end face of the distal end rigid portion 10.

A distal end side of a treatment instrument insertion channel 25 that has a function as a fluid conduit is communicated with the suction and forceps port 22. In order to dispose a treatment instrument that is led out from the suction and forceps port 22 within a scanning region As of the ultrasound probe 17 and to also exert a favorable suction force in the vicinity of the ultrasound probe 17, the suction and forceps port 22 is disposed in the distal end face of the distal end rigid portion 10 so that a central axis O1 thereof is positioned on an extension line in the scanning direction (center line L1) of the ultrasound probe 17 (see FIG. 5). Further, on the distal end face 10a of the distal end rigid portion 10, the observation window 20, the illuminating window 21a and the air/water feeding nozzle 23 are disposed together on one side of the suction and forceps port 22, and the illuminating window 21b and auxiliary water feeding channel port 24 are disposed together on the other side of the suction and forceps port 22.

As shown in FIG. 1, an angle knob 30 for performing an operation to bend the bending portion 11 in a desired direction, an air/water feeding button 31 for performing operations to feed air and water, a suction button 32 for performing a suction operation, a plurality of button switches 33 that can be allocated to arbitrary functions among various functions relating to the endoscope 2, and a treatment instrument insertion port 34 that serves as an entry port for a treatment instrument that is introduced into the body are arranged in the operation portion 6. In the present embodiment it is possible to set any of the button switches 33 as, for example, a switch for instructing the start and end of an elastography observation using the ultrasound unit 15. Further, the treatment instrument insertion port 34 is communicated with the treatment instrument insertion channel 25 (see FIGS. 2 and 3) that extends from inside the insertion portion 5.

One end side of the universal cord 7 is connected via the bend preventing portion 40 with a side portion of the operation portion 6. On the other hand, a scope connector portion 41 is provided at an extending end that is the other end side of the universal cord 7. A light source-side connector 42 that is detachably attachable to an unshown light source apparatus is provided at an end portion of the scope connector portion 41. Proximal end portions of a light guide 42a and an air feeding tube 42b that extend from the insertion portion 5 side are provided in a protruding condition in the light source-side connector 42, and unshown electric contacts are also arranged in the light source-side connector 42. An ultrasound connector 43 that is detachably attachable to an ultrasound observation apparatus 50, and an electrical connector 44 that is detachably attachable to an unshown video processor are provided side-by-side on one side portion of the scope connector portion 41. Further, on the one side portion of the scope connector portion 41, a suction pipe sleeve 47 that is detachably attachable to a suction apparatus 55 is provided between the ultrasound connector 43 and the electrical connector 44. In addition, on the other side portion of the scope connector portion 41, proximal end portions of a pressurization tube 45a and a water feeding tube 45b are provided in a protruding condition, and an auxiliary water feeding pipe sleeve 46 that is detachably attachable to a fluid feeding apparatus for an ultrasound endoscope (not illustrated in the drawings) is also provided.

As shown in FIGS. 2 and 3, the suction pipe sleeve 47 is communicated with the treatment instrument insertion channel 25 through a suction channel 48 as a fluid conduit. Further, for example, inside the scope connector portion 41, a regulating valve 49 as a first flow rate regulating portion is interposed partway along the suction channel 48. The regulating valve 49 is constituted by, for example, a normally-closed electromagnetic solenoid valve. By controlling an open time period of the regulating valve 49 according to an arbitrary duty ratio, a negative pressure for suction that is transmitted to the suction and forceps port 22 through the suction channel 48 and the treatment instrument insertion channel 25 can be controlled to an arbitrary state. More specifically, for example, by performing periodic duty-control of the open time period of the regulating valve 49 according to an arbitrary duty ratio, it is possible to change a negative pressure for suction that is transmitted to the suction and forceps port 22 to two or more arbitrary states (for example, it is possible to periodically change the negative pressure for suction to an arbitrary two states). Note that it is also possible to provide the regulating valve 49 inside the operation portion 6 instead of inside the scope connector portion 41. As used herein, the meaning of the term "negative pressure for suction" also includes a state in which a negative pressure is zero (atmospheric pressure).

As shown in FIGS. 1 to 3, the suction apparatus 55 of the present embodiment includes a pump unit 56 configured to generate a negative pressure for suction, and a trap container 57 that is provided side-by-side with the pump unit 56. The pump unit 56 has a peristaltic pump 60. The peristaltic pump 60 is communicated with an upper portion of the trap container 57 through a negative pressure tube 61. Further, one end of a negative pressure tube 62 is disposed so as to face the bottom of the trap container 57, and the other end of the negative pressure tube 62 is connected to the suction channel 48 through the suction pipe sleeve 47. In the suction apparatus 55, when the peristaltic pump 60 of the pump unit 56 is driven, a negative pressure (negative pressure for suction) generated by the peristaltic pump is transmitted to the inside of the suction channel 48 through the negative pressure tube 61 and the trap container 57. That is, in the present embodiment, the peristaltic pump 60 realizes a function as a negative pressure generation portion.

As shown in FIG. 1, the ultrasound observation apparatus 50 is connected to the ultrasound connector 43 through an ultrasound connection cable 51. The ultrasound observation apparatus 50 performs driving control of the ultrasound probe 17, and generates various ultrasound images based on ultrasound echo signals (ultrasound signals) received with the ultrasound probe 17 according to the driving control. For example, the ultrasound observation apparatus 50 is capable of generating B-mode images in which the amplitude of a received ultrasound echo signal is correlated with a luminance and the like.

Further, for example, when an instruction to start an elastography observation is issued by operation of the button switch 33 or the like by a user or the like, the ultrasound observation apparatus 50 drives the peristaltic pump 60 and, through control of the regulating valve 49, also regulates a negative pressure that is transmitted to the suction channel 48. By this means, a negative pressure for suction that is transmitted to the suction and forceps port 22 through the suction channel 48 and the treatment instrument insertion channel 25 changes. A suction force produced by the negative pressure for suction is a force for sucking living tissue present in the vicinity of the ultrasound probe 17 in an opposite direction to the protruding direction of the ultrasound probe 17. Hence, by the action of the negative pressure for suction, a pressing force with which the ultrasound probe 17 presses the living tissue indirectly changes without moving the ultrasound probe 17. As a result, it is possible for the ultrasound probe 17 to obtain ultrasound signals in different pressing states. Further, the ultrasound observation apparatus 50 measures a change (displacement) in a deformed state of the living tissue based on the ultrasound signals in the different pressing states, and generates an elastographic image based on the result of measuring the displacement.

As a specific example, referring to FIGS. 2 and 3 a case will be described of performing elastography observation of a pancreas 101 through a gastric wall 100 in order to perform an examination for tumor/lymph node metastasis or the like in the pancreas 101. First, prior to observation, the distal end rigid portion 10 of the endoscope 2 that is inserted into a body cavity is disposed at a position at which the distal end rigid portion 10 presses against the gastric wall 100 and the pancreas 101 through the ultrasound probe 17 with a predetermined weak pressing force. Further, the peristaltic pump 60 is driven and the regulating valve 49 is duty-controlled by the ultrasound observation apparatus 50. By this means, for example, a state in which a negative pressure for suction is not transmitted to the suction and forceps port 22 (see FIG. 2) and a state in which a predetermined negative pressure for suction is transmitted to the suction and forceps port 22 (see FIG. 3) are periodically repeated. In this case, in a state in which a negative pressure for suction is being transmitted to the suction and forceps port 22, living tissue in the vicinity of the ultrasound probe 17 is drawn in by the negative pressure. As a result, the pressing force of the ultrasound probe 17 with respect to the gastric wall 100 and the like is increased without moving the ultrasound probe 17 relative to the gastric wall 100 and the like. That is, a pressing force of the ultrasound probe 17 with respect to the gastric wall 100 and the like periodically changes between a pressing force (first pressing force) when a negative pressure for suction is not being transmitted to the suction and forceps port 22 and a pressing force (second pressing force that is stronger than the first pressing force) when a negative pressure for suction is being transmitted to the suction and forceps port 22. Further, each time the pressing force of the ultrasound probe 17 with respect to the gastric wall 100 and the like changes between the first pressing force and the second pressing force, the ultrasound observation apparatus 50 acquires an ultrasound signal in the corresponding pressing state by performing driving control of the ultrasound probe 17 (ultrasound transducer 17a).

According to the present embodiment that is described above, by having the ultrasound probe 17 that is arranged in the distal end rigid portion 10, the suction and forceps port 22 provided in the vicinity of the ultrasound probe 17, the treatment instrument insertion channel 25 and the suction channel 48 which communicate with the suction and forceps port 22, and the regulating valve 49 that variably regulates a negative pressure for suction which is transmitted to the suction and forceps port 22 through the treatment instrument insertion channel 25 and the suction channel 48 in two or more states, favorable elastographic images can be obtained by means of a simple configuration without making the distal end portion a large size.

That is, by adopting a configuration which, by sucking living tissue in the vicinity of the ultrasound probe 17 by means of negative pressure for suction that is transmitted to the suction and forceps port 22, results in the ultrasound probe 17 being caused to press the living tissue, favorable elastographic images can be obtained by means of a simple configuration without providing a pressing mechanism or the like for mechanically pressing a body cavity in the distal end rigid portion 10 of the endoscope 2. In particular, since a pressing force towards the living tissue is a force caused by suction, the cohesiveness between the ultrasound probe 17 and the living tissue can be increased, and favorable elastographic images can be obtained.

In this case, by disposing the suction and forceps port 22 on an extension line in the scanning direction (center line L1) of the ultrasound probe 17, living tissue such as the gastric wall 100 can be efficiently pressed against the acoustic lens 17b by means of the negative pressure for suction.

Figure 6:
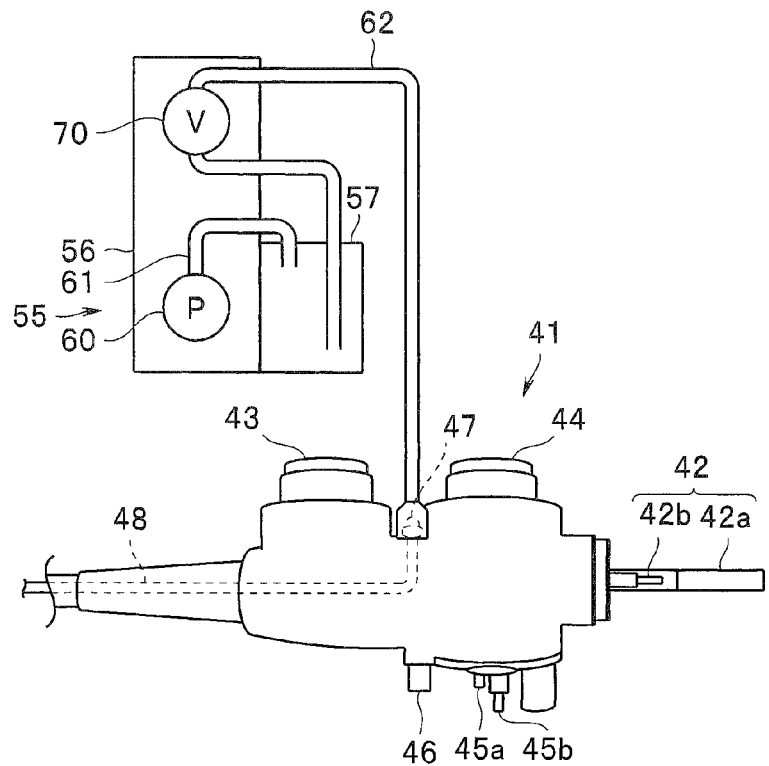
FIG. 6 is a schematic configuration diagram of a suction apparatus for an ultrasound endoscope according to a second embodiment of the present invention.

Next, FIG. 6 relates to a second embodiment of the present invention. FIG. 6 is a schematic configuration diagram of a suction apparatus for an ultrasound endoscope. Note that, the present embodiment mainly differs from the above described first embodiment in that instead of the regulating valve 49 as the first flow rate regulating portion that is arranged on the endoscope 2 side in the first embodiment, in the present embodiment a regulating valve 70 as a second flow rate regulating portion is arranged on the side of the suction apparatus 55 for an ultrasound endoscope. Note that, components which are the same as in the above described first embodiment are denoted by the same reference numerals and a description thereof is omitted as appropriate.

As shown in FIG. 6, the regulating valve 70 of the present embodiment, for example, is interposed partway along the negative pressure tube 62 in the pump unit 56.

The regulating valve 70 is constituted by, for example, a normally-closed electromagnetic solenoid valve. By controlling an open time period of the regulating valve 70 according to an arbitrary duty ratio, it is possible for the ultrasound observation apparatus 50 to control a negative pressure for suction that is transmitted to the suction channel 48 to an arbitrary state. More specifically, for example, by performing periodic duty-control of the open time period of the regulating valve 70 according to an arbitrary duty ratio, it is possible to change a negative pressure for suction that is transmitted to the suction channel 48 to an arbitrary plurality of states (for example, it is possible to periodically change the negative pressure for suction between two arbitrary states).

According to the present embodiment configured in this manner, substantially the same working effect as in the above-described first embodiment can be exhibited. In addition, in the present embodiment, by providing the regulating valve 70 inside the suction apparatus 55 for an ultrasound endoscope, favorable elastographic images can be obtained with the endoscope 2 that includes the suction and forceps port 22 and the like, without making any kind of design changes or the like.

In the present embodiment, various modifications are possible as configurations for performing flow rate regulation by means of the suction apparatus 55 for an ultrasound endoscope.

Figure 7:
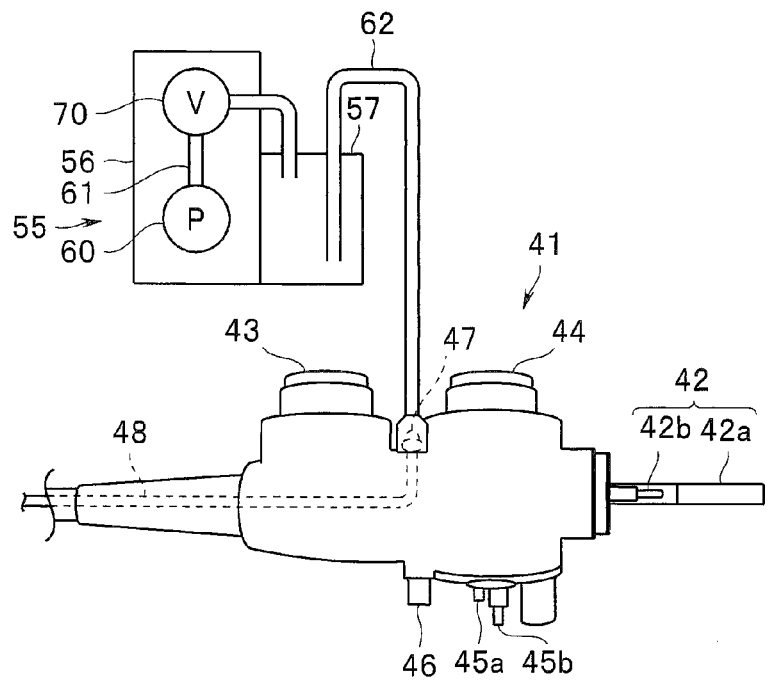
FIG. 7 is a schematic configuration diagram of a suction apparatus for an ultrasound endoscope according to a first modification of the second embodiment of the present invention.

For example, instead of the configuration in which the regulating valve 70 is interposed along the negative pressure tube 62, as shown in FIG. 7 it is also possible to interpose the regulating valve 70 as the second flow rate regulating portion partway along the negative pressure tube 61.

Figure 8:
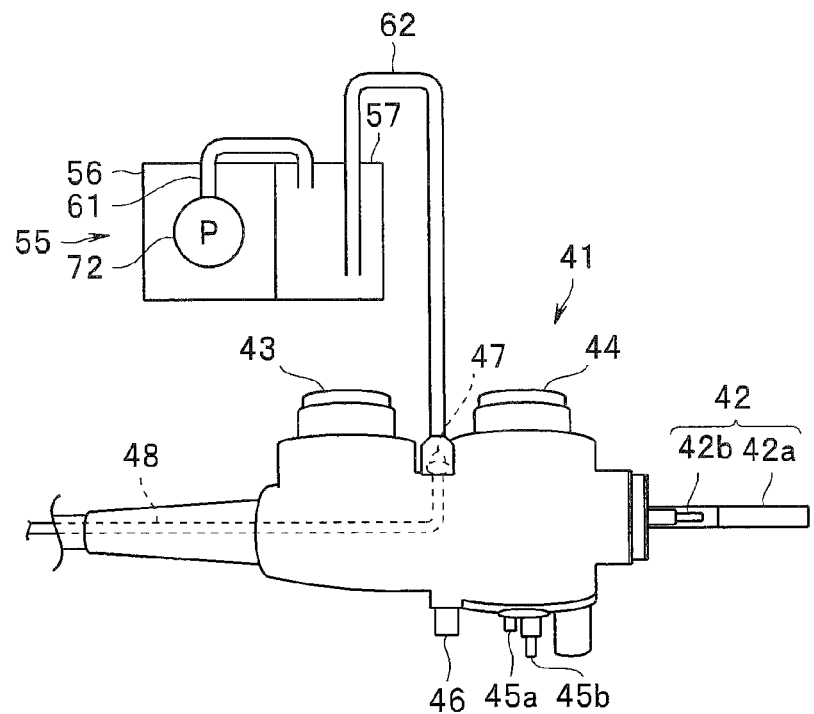
FIG. 8 is a schematic configuration diagram of a suction apparatus for an ultrasound endoscope according to a second modification of the second embodiment of the present invention.
Figure 9:
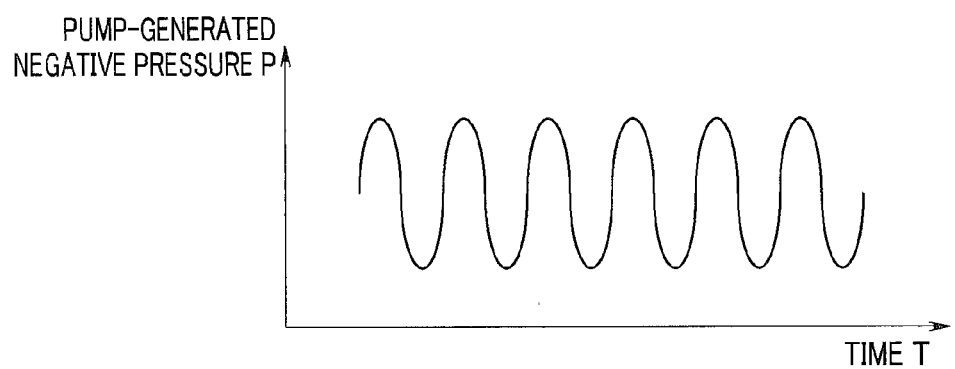
FIG. 9 is a time chart illustrating a pump-generated negative pressure according to the second modification of the second embodiment of the present invention.

Further, for example, as shown in FIG. 8, it is also possible to adopt a positive displacement pump 72 as the pump included in the pump unit 56 instead of the peristaltic pump 60. In this case, for example, as shown in FIG. 9, since the positive displacement pump 72 included in the pump unit 56 is originally a pump with respect to which a predetermined pulsation accompanies generation of a negative pressure, a negative pressure for suction that is transmitted to the suction channel 48 can be periodically changed without using a regulating valve. That is, in the modification illustrated in FIG. 8, the positive displacement pump 72 itself realizes a function as a fluid lead-out portion and a second flow rate regulating portion. Note that, in this configuration, it is desirable to set the volume of the trap container 57 or the like to be as small an amount as possible so as to suppress attenuation of a negative pressure generated by the positive displacement pump 72.

Figure 10:
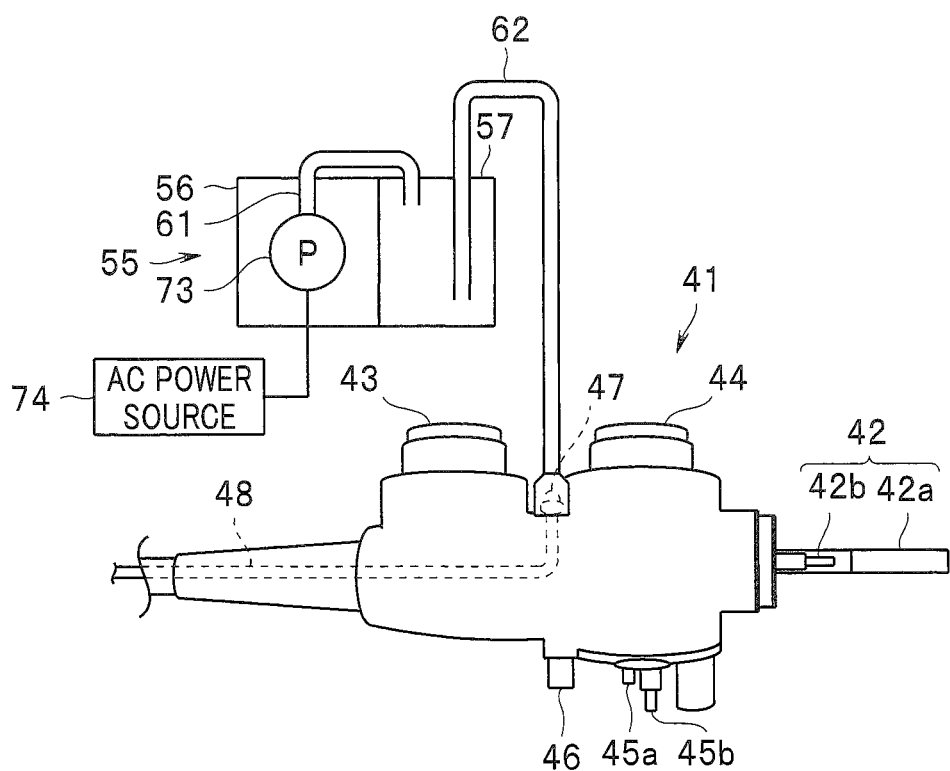
FIG. 10 is a schematic configuration diagram of a suction apparatus for an ultrasound endoscope according to a third modification of the second embodiment of the present invention.

Alternatively, instead of providing the positive displacement pump 72, for example, as shown in FIG. 10, it is also possible to adopt a DC pump 73 as the pump included in the pump unit 56 and to periodically change an output voltage by utilizing an AC power source 74 as means for supplying power to the DC pump 73, and to thereby periodically change a negative pressure for suction that is transmitted to the suction channel 48 without using a regulating valve. In addition, a power supply control portion may be interposed between the DC pump 73 and the AC power source 74, and the voltage cycle of the AC power supply may be modulated.

Figure 11:
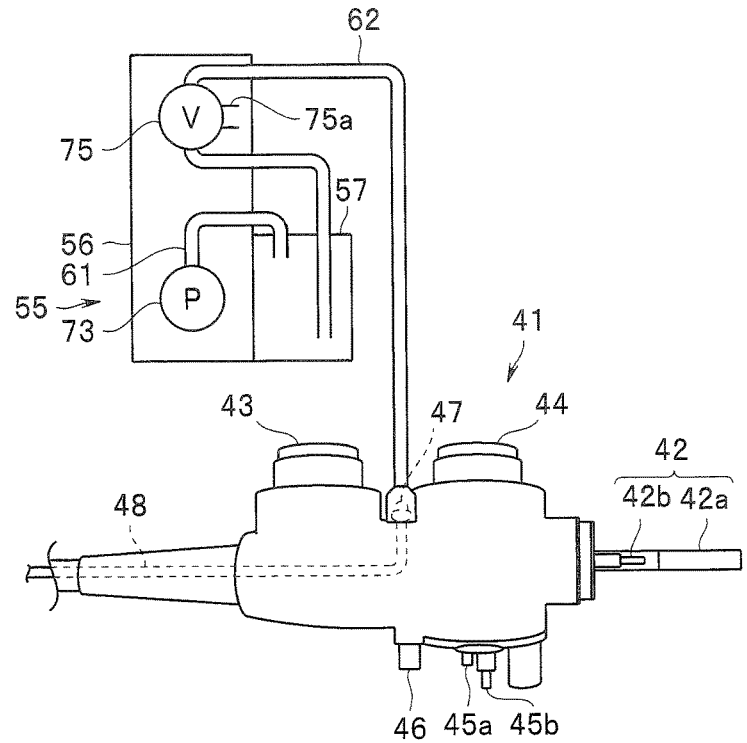
FIG. 11 is a schematic configuration diagram of a suction apparatus for an ultrasound endoscope according to a fourth modification of the second embodiment of the present invention.

Further, for example, as shown in FIG. 11, a configuration may also be adopted in which, on the downstream side of the DC pump 73, a relief valve 75 as the second flow rate regulating portion is interposed partway along the negative pressure tube 62, and a negative pressure transmitted from the DC pump 73 is changed by a mechanical action of the relief valve 75. That is, in such a configuration, for example, the DC pump 73 is driven so as to generate a predetermined high negative pressure. Further, when the internal pressure of the negative pressure tube 62 between the DC pump 73 and an atmosphere release passage 75a is reduced and becomes equal to or greater than a predetermined high negative pressure, the relief valve 75 mechanically opens the atmosphere release passage 75a, and by this means the negative pressure in the negative pressure tube 62 between the DC pump 73 and the atmosphere release passage 75a decreases. On the other hand, when the internal pressure of the negative pressure tube 62 between the DC pump 73 and the atmosphere release passage 75a becomes less than a predetermined low negative pressure as a result of opening the atmosphere release passage 75a, the relief valve 75 mechanically blocks the atmosphere release passage 75a, and by this means the negative pressure of the negative pressure tube 62 rises again. By the relief valve 75 repeating such operations, the flow rate of a fluid flowing through the suction channel 48 is periodically changed.

Figure 12:
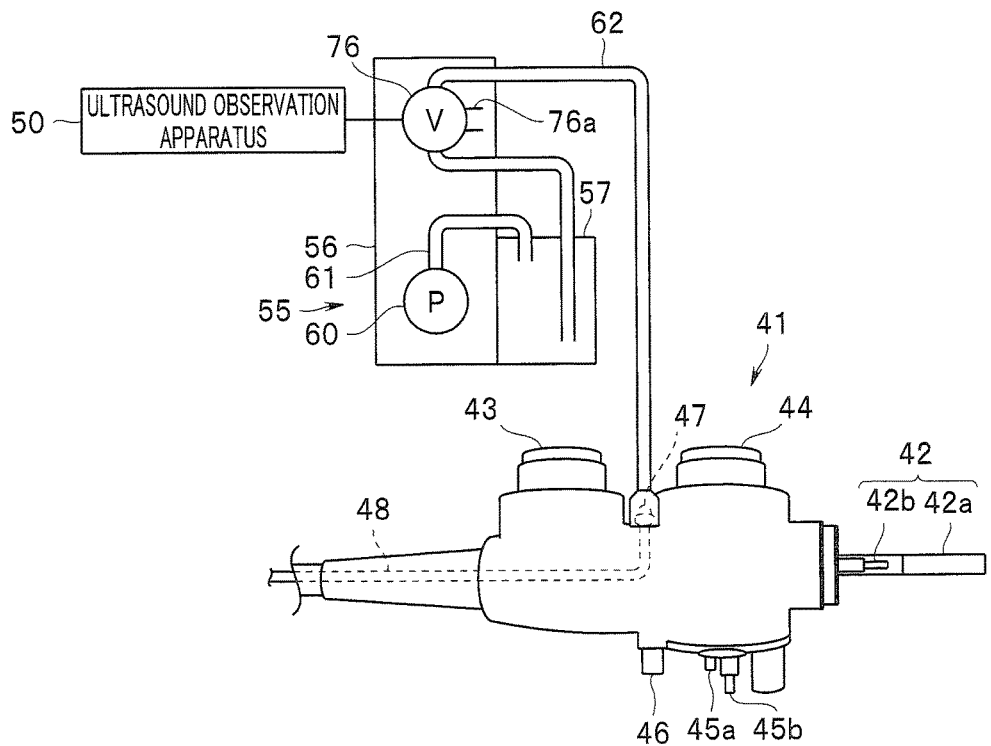
FIG. 12 is a schematic configuration diagram of a suction apparatus for an ultrasound endoscope according to a fifth modification of the second embodiment of the present invention.

Furthermore, for example, as shown in FIG. 12, it is also possible to change the negative pressure that is generated at the DC pump 73 by interposing a three-way valve 76 as a second flow rate regulating portion partway along the negative pressure tube 62 on the downstream side of the DC pump 73, and controlling the three-way valve 76 by means of the ultrasound observation apparatus 50 or the like. That is, in such a configuration, by performing control with respect to the three-way valve 76, the ultrasound observation apparatus 50 periodically connects the DC pump 73 to the downstream side of the negative pressure tube 62 and to the atmosphere release passage 76a in an alternating manner. As a result, a negative pressure transmitted to the suction channel 48 periodically changes.

Figure 13:
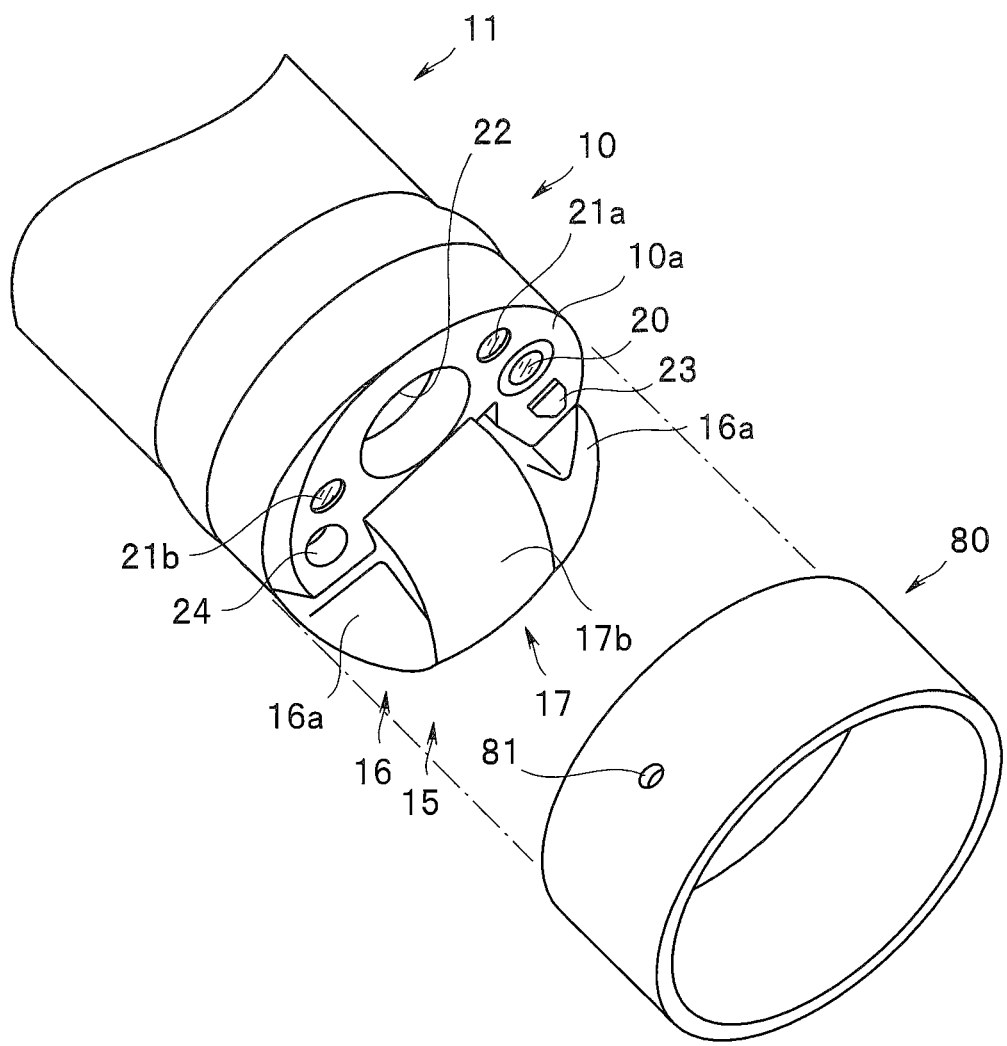
FIG. 13 is an exploded perspective view illustrating a distal end portion and a cap according to a third embodiment of the present invention.
Figure 14:
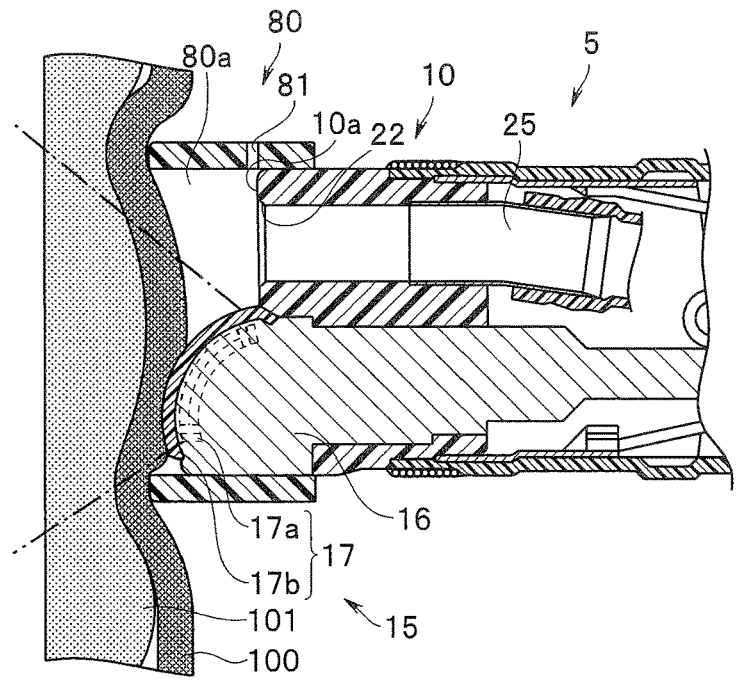
FIG. 14 is an explanatory drawing that schematically illustrates a relation between an ultrasound probe and a gastric wall when suction is not performed according to the third embodiment of the present invention.
Figure 15:
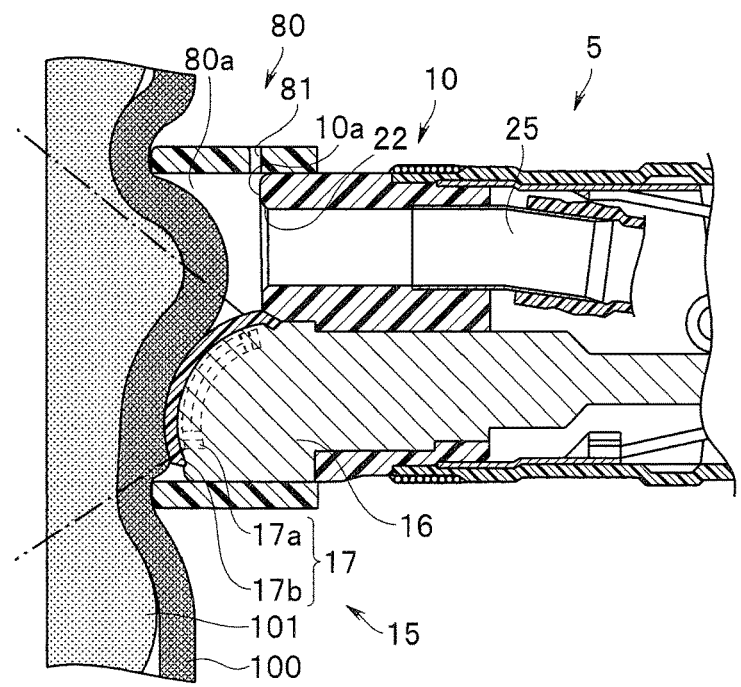
FIG. 15 is an explanatory drawing that schematically illustrates a relation between an ultrasound probe and a gastric wall when suction is performed according to the third embodiment of the present invention.

Next, FIGS. 13 to 15 relate to a third embodiment of the present invention, among which FIG. 13 is an exploded perspective view illustrating a distal end portion and a cap, FIG. 14 is an explanatory drawing that schematically illustrates a relation between an ultrasound probe and a gastric wall when suction is not performed, and FIG. 15 is an explanatory drawing that schematically illustrates a relation between an ultrasound probe and a gastric wall when suction is performed. Note that, the present embodiment mainly differs from the above described first and second embodiments in the respect that a cap 80 is mounted to the distal end rigid portion 10 of the endoscope 2 in order to improve the suction efficiency with respect to a subject such as living tissue. Note that, components which are the same as in the above described first and second embodiments are denoted by the same reference numerals and a description thereof is omitted as appropriate.

As shown in FIG. 13 to FIG. 15, in the present embodiment a tubular cap 80 is detachably mounted by fitting or the like to the outer circumference of the distal end side of the distal end rigid portion 10. More specifically, the cap 80 is constituted by a cylindrical member made of a rigid resin or the like. The cap 80 is mounted to the distal end rigid portion 10 so as to surround the ultrasound probe 17 and the suction and forceps port 22 as a result of the proximal end side of the cap 80 being fitted to the exterior of the distal end rigid portion 10 so that the distal end side of the cap 80 protrudes more than the distal end face 10a. The cap 80 forms a negative pressure chamber 80a (see FIGS. 14 and 15) between the distal end rigid portion 10 and the subject when the ultrasound probe 17 is brought into contact with the subject, and negative pressure for suction that is introduced through the suction and forceps port 22 can be stored inside the negative pressure chamber 80a.

In this case, a minute leak hole 81 for allowing the inside and outside of the negative pressure chamber 80a to communicate is formed in the peripheral wall of the cap 80. Note that it is possible to appropriately omit the leak hole 81.

As a specific example of elastography observation using the cap, referring to FIGS. 14 and 15 a case will now be described of performing elastography observation with respect to the pancreas 101 through the gastric wall 100 in order to perform an examination for tumor/lymph node metastasis or the like in the pancreas 101. First, prior to the observation, the distal end rigid portion 10 of the endoscope 2 that is inserted into a body cavity is disposed at a position at which the distal end rigid portion 10 presses against the gastric wall 100 and the pancreas 101 through the ultrasound probe 17 with a predetermined weak pressing force. By this means, the negative pressure chamber 80a that communicates with the suction and forceps port 22 and surrounds the ultrasound probe 17 is formed between the cap 80 and the gastric wall 100. Next, the peristaltic pump 60 is driven and the regulating valve 49 is duty-controlled by the ultrasound observation apparatus 50. By this means, for example, a state in which a negative pressure for suction is not being transmitted to the suction and forceps port 22 (see FIG. 14) and a state in which a predetermined negative pressure for suction is being transmitted to the suction and forceps port 22 (see FIG. 15) are periodically repeated.

In this case, in a state in which a negative pressure for suction is being transmitted to the suction and forceps port 22, the negative pressure for suction is stored inside the negative pressure chamber 80a, and living tissue in the vicinity of the ultrasound probe 17 is drawn in by the stored negative pressure. As a result, the pressing force of the ultrasound probe 17 with respect to the gastric wall 100 and the like is increased without moving the ultrasound probe 17 relative to the gastric wall 100 and the like. At this time, a sudden rise in the negative pressure inside the negative pressure chamber 80a is prevented by the action of the leak hole 81, and thus a sudden increase in the pressing force of the ultrasound probe 17 with respect to the gastric wall 100 and the like is suppressed. On the other hand, when introduction of the negative pressure for suction into the negative pressure chamber 80a through the suction and forceps port 22 is stopped, the negative pressure for suction that had been stored inside the negative pressure chamber 80a is rapidly discharged through the leak hole 81, and as a result the pressing force of the ultrasound probe 17 on the gastric wall 100 and the like decreases. Thus, the pressing force of the ultrasound probe 17 on the gastric wall 100 and the like periodically changes between a pressing force (first pressing force) at a time that a negative pressure for suction is not transmitted to the suction and forceps port 22 and a pressing force (a second pressing force that is stronger than the first pressing force) at a time that a negative pressure for suction is transmitted to the suction and forceps port 22. Further, each time the pressing force of the ultrasound probe 17 on the gastric wall 100 and the like changes between the first pressing force and the second pressing force, the ultrasound observation apparatus 50 acquires an ultrasound signal in the corresponding pressing state by performing driving control of the ultrasound probe 17 (ultrasound transducer 17a).

According to this embodiment, by mounting the cap 80 to the distal end rigid portion 10 to form the negative pressure chamber 80a between the distal end rigid portion 10 and the subject, it is possible to effectively realize control of a pressing force that utilizes a negative pressure for suction.

In the present embodiment, various modifications are possible with respect to the configuration of the cap that is mounted to the distal end rigid portion 10.

Figure 16:
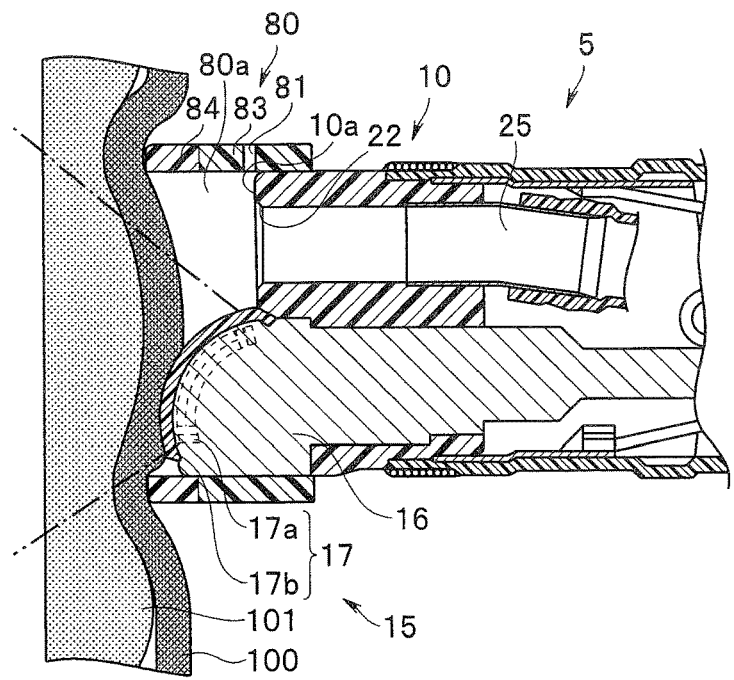
FIG. 16 is an explanatory drawing that schematically illustrates a relation between an ultrasound probe and a gastric wall when suction is not performed according to a first modification of the third embodiment of the present invention.
Figure 17:
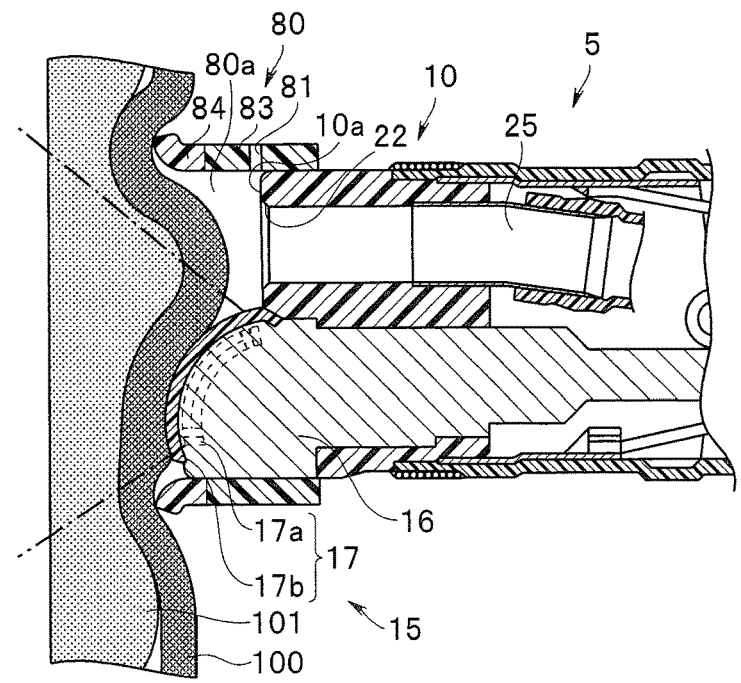
FIG. 17 is an explanatory drawing that schematically illustrates a relation between an ultrasound probe and a gastric wall when suction is performed according to a first modification of the third embodiment of the present invention.

For example, as shown in FIGS. 16 and 17, the cap 80 can also be formed by connecting a flexible tubular portion 84 made of a flexible resin or the like to a distal end of a rigid tubular portion 83 made of a rigid resin or the like. In this configuration, the flexible tubular portion 84 elastically deforms in accordance with a negative pressure state inside the negative pressure chamber 80a. The entire length of the cap 80 is expanded or contracted depending on the elastic deformation, and as a result it is possible to realize an advancing and retracting motion with respect to an insertion axis direction of the distal end rigid portion 10. Further, when a negative pressure for suction is introduced into the negative pressure chamber 80a and the flexible tubular portion 84 is contracted, because the distal end rigid portion 10 moves towards the side of the subject such as the gastric wall 100 in response to the contracting action, the gastric wall 100 or the like can be pressed more effectively by the ultrasound probe 17. That is, by a synergistic effect of the movement of the gastric wall 100 and the like and movement of the distal end rigid portion 10 which are caused by the negative pressure for suction, the gastric wall 100 and the like can be effectively pressed by the ultrasound probe 17. In this case, because the flexible tubular portion 84 elastically expands and contracts, abrupt fluctuations in the pressing force produced by the ultrasound probe 17 can be suppressed by a damper effect thereof. In addition, the load placed on the subject is reduced by contact of the flexible tubular portion 84 of the cap 80 of the present modification against the subject, and the cap 80 can be caused to contact against the subject with a high degree of cohesiveness.

Figure 18:
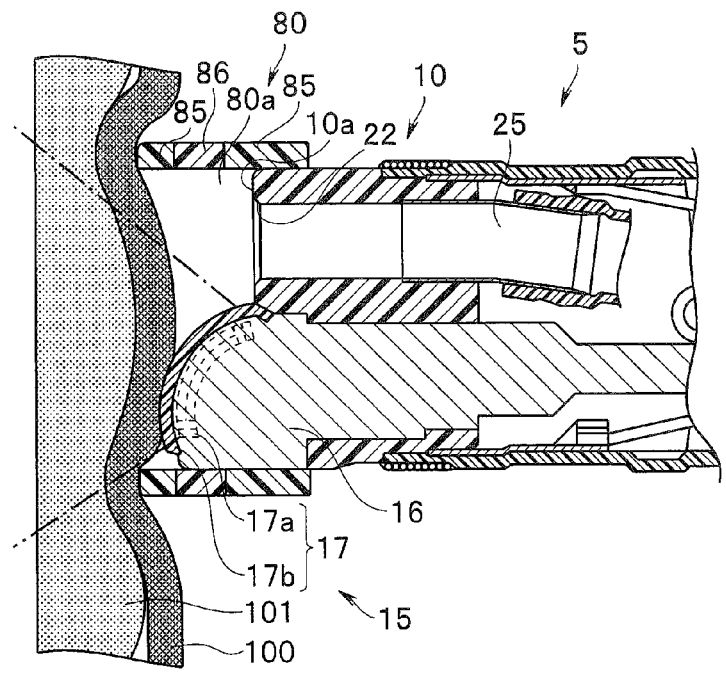
FIG. 18 is an explanatory drawing that schematically illustrates a relation between an ultrasound probe and a gastric wall when suction is not performed according to a second modification of the third embodiment of the present invention.
Figure 19:
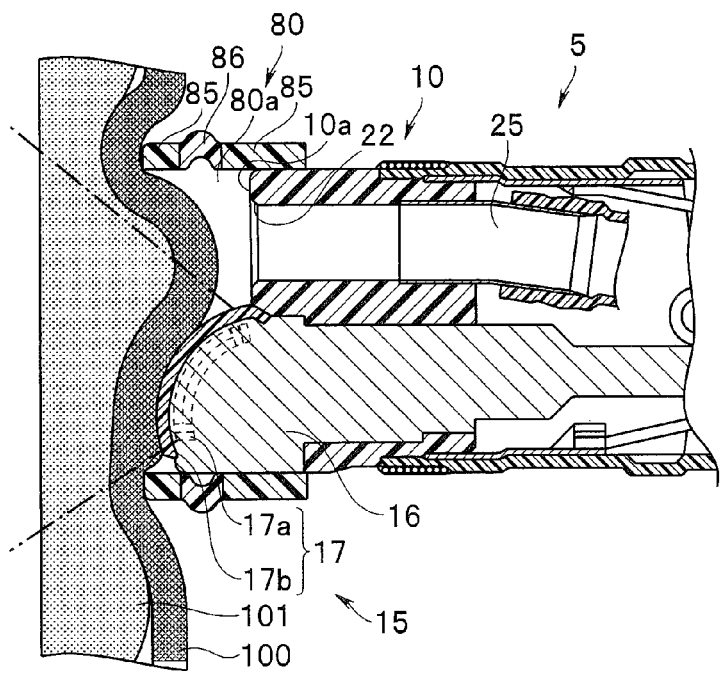
FIG. 19 is an explanatory drawing that schematically illustrates a relation between an ultrasound probe and a gastric wall when suction is performed according to a second modification of the third embodiment of the present invention.

Alternatively, for example, as shown in FIGS. 18 and 19, the cap 80 can also be formed by interposing a flexible tubular portion 86 made of a flexible resin or the like partway along a rigid tubular portion 85 made of a rigid resin or the like. In this configuration, the flexible tubular portion 86 elastically deforms in accordance with a negative pressure state inside the negative pressure chamber 80a. The entire length of the cap 80 is expanded or contracted depending on such elastic deformation, and as a result it is possible to realize an advancing and retracting motion with respect to the insertion axis direction of the distal end rigid portion 10. Further, when a negative pressure for suction is introduced into the negative pressure chamber 80a and the flexible tubular portion 86 is contracted, because the distal end rigid portion 10 moves towards the side of the subject such as the gastric wall 100 in response to the contracting action, the gastric wall 100 or the like can be pressed more effectively by the ultrasound probe 17. In this case, because the flexible tubular portion 86 elastically expands and contracts, abrupt fluctuations in the pressing force produced by the ultrasound probe 17 can be suppressed by a damper effect thereof. In addition, after accurately performing positioning of the cap 80 of the present modification with respect to the subject by means of the distal end of the rigid tubular portion 85, an inclination or the like of the distal end rigid portion 10 with respect to the subject can be absorbed by the flexible tubular portion 86, and thus stable pressing motions can be realized.

Figure 20:
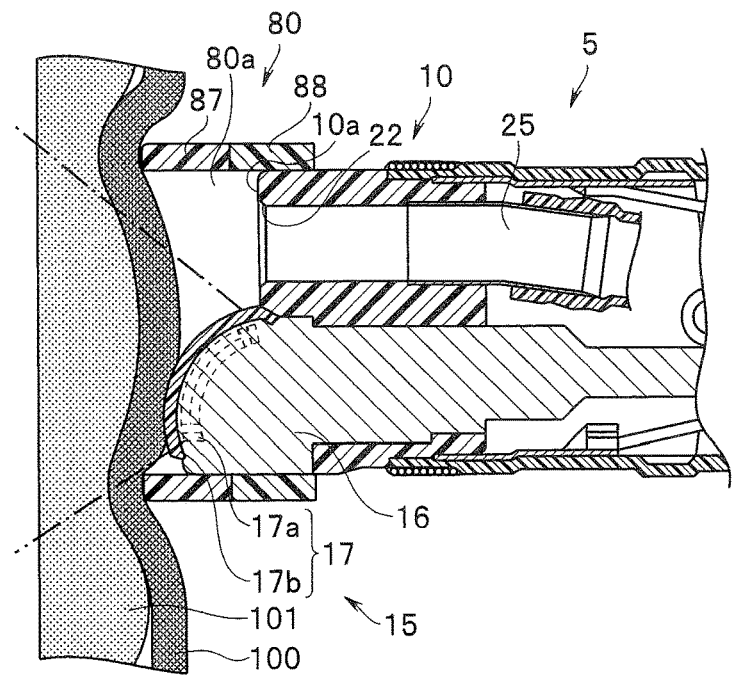
FIG. 20 is an explanatory drawing that schematically illustrates a relation between an ultrasound probe and a gastric wall when suction is not performed according to a third modification of the third embodiment of the present invention.
Figure 21:
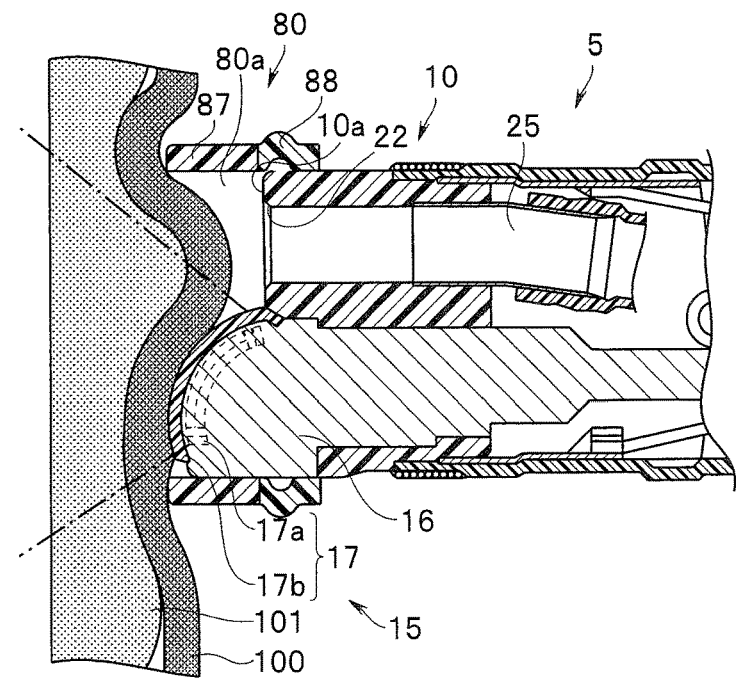
FIG. 21 is an explanatory drawing that schematically illustrates a relation between an ultrasound probe and a gastric wall when suction is performed according to a third modification of the third embodiment of the present invention.

Alternatively, for example, as shown in FIGS. 20 and 21, it is also possible to form the cap 80 by connecting a flexible tubular portion 88 made of a flexible resin or the like to the proximal end of a rigid tubular portion 87 made of a rigid resin or the like. In this configuration, the flexible tubular portion 88 elastically deforms in accordance with a negative pressure state inside the negative pressure chamber 80a. The entire length of the cap 80 is expanded or contracted depending on such elastic deformation, and as a result it is possible to realize an advancing and retracting motion with respect to the insertion axis direction of the distal end rigid portion 10. In this case, because the flexible tubular portion 88 elastically expands and contracts, abrupt fluctuations in the pressing force produced by the ultrasound probe 17 can be suppressed by a damper effect thereof. In addition, because the flexible tubular portion 88 of the cap 80 of the present modification fits to the outer circumference of the distal end rigid portion 10, the airtightness of the cap 80 with respect to the distal end rigid portion 10 can be enhanced.

Figure 22:
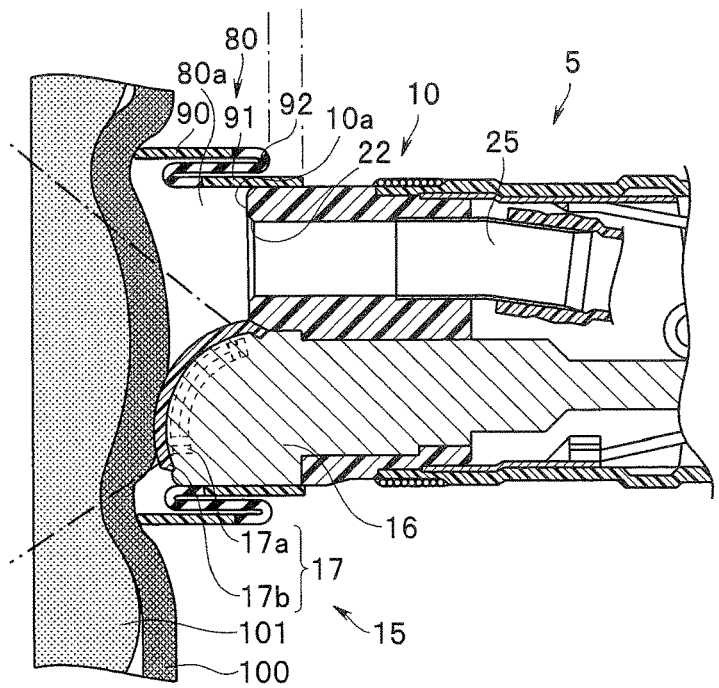
FIG. 22 is an explanatory drawing that schematically illustrates a relation between an ultrasound probe and a gastric wall when suction is not performed according to a fourth modification of the third embodiment of the present invention.
Figure 23:
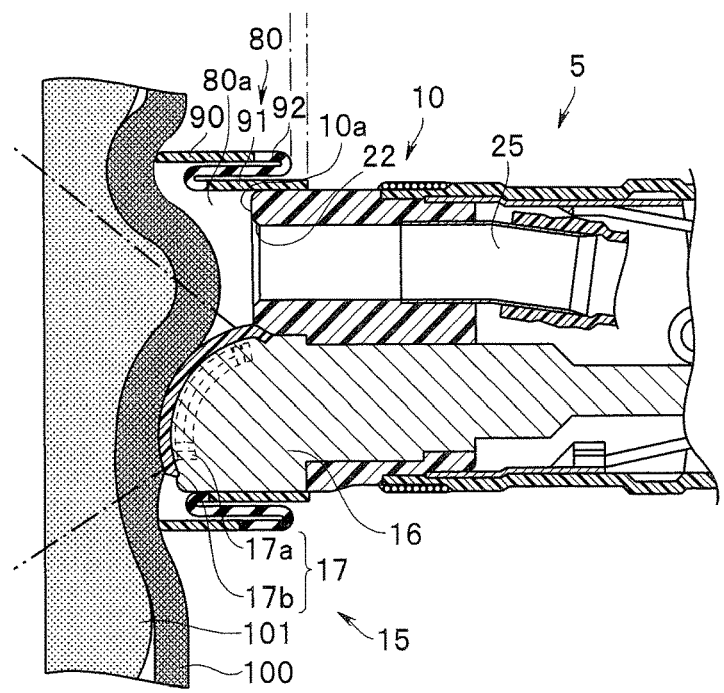
FIG. 23 is an explanatory drawing that schematically illustrates a relation between an ultrasound probe and a gastric wall when suction is performed according to a fourth modification of the third embodiment of the present invention.

Alternatively, for example, as shown in FIGS. 22 and 23, the cap 80 can be formed by disposing first and second rigid tubular portions 90 and 91, which are made of a rigid resin or the like, so that outer and inner faces thereof in a radial direction overlap and connecting between the first and second rigid tubular portions 90 and 91 by a flexible tubular portion 92 made of a flexible resin or the like. According to this configuration, by the second rigid tubular portion 91 being guided by the first rigid tubular portion 90 that contacts against the subject, pressing motions produced by the ultrasound probe 17 can be efficiently realized without causing deviation of the insertion axis when introducing negative pressure for suction or the like.

Figure 24:
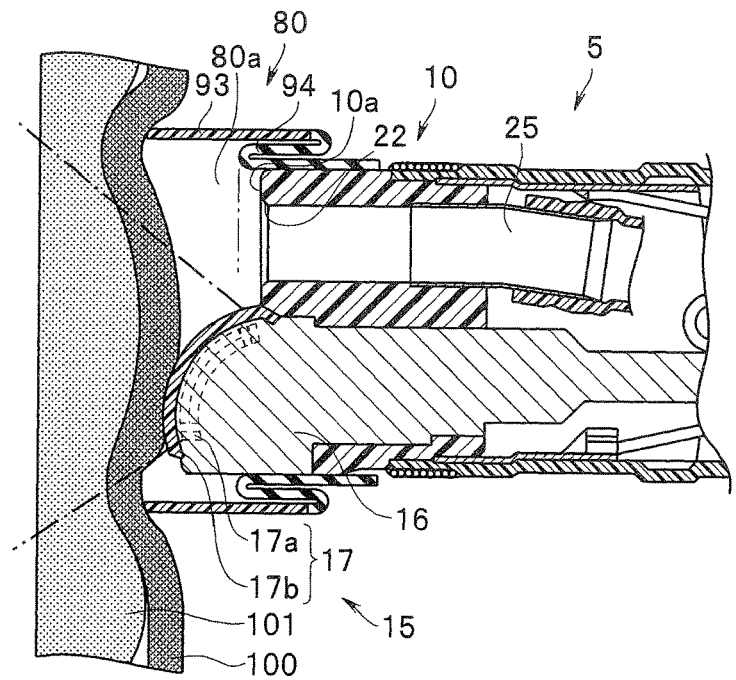
FIG. 24 is an explanatory drawing that schematically illustrates a relation between an ultrasound probe and a gastric wall when suction is not performed according to a fifth modification of the third embodiment of the present invention.
Figure 25:
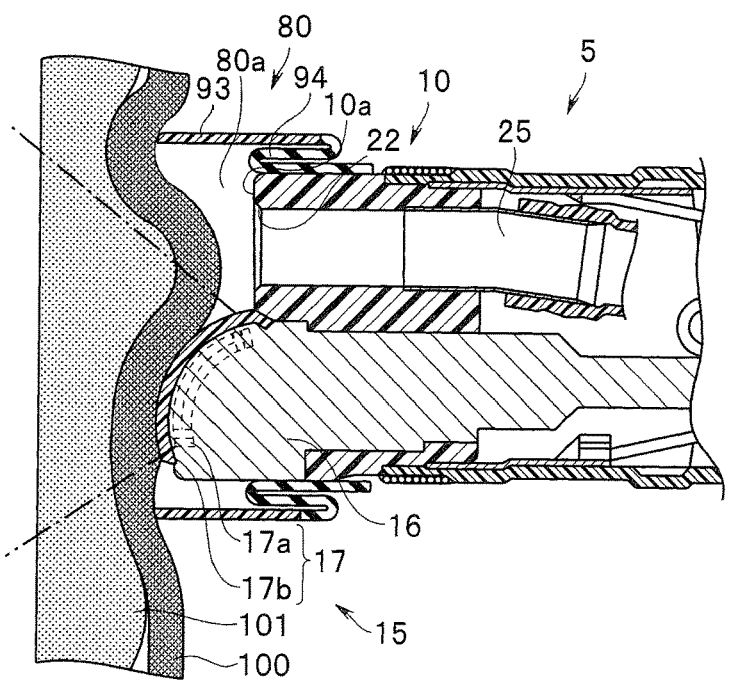
FIG. 25 is an explanatory drawing that schematically illustrates a relation between an ultrasound probe and a gastric wall when suction is performed according to a fifth modification of the third embodiment of the present invention.

Alternatively, for example, as shown in FIGS. 24 and 25, it is also possible to form the cap 80 by connecting a flexible tubular portion 94 which is made of a flexible resin and which can be folded back (is foldable) multiple times in the radial direction of the distal end rigid portion 10 to the proximal end of a rigid tubular portion 93 made of a rigid resin or the like. According to this configuration, by the outer circumference of the distal end rigid portion 10 that is covered by the flexible tubular portion 94 being guided by the rigid tubular portion 93 that contacts against the subject, pressing actions produced by the ultrasound probe 17 can be efficiently realized without causing deviation of the insertion axis when introducing negative pressure for suction or the like. Further, because the flexible tubular portion 94 fits to the outer circumference of the distal end rigid portion 10, the airtightness of the cap 80 with respect to the distal end rigid portion 10 can be enhanced.

Figure 26:
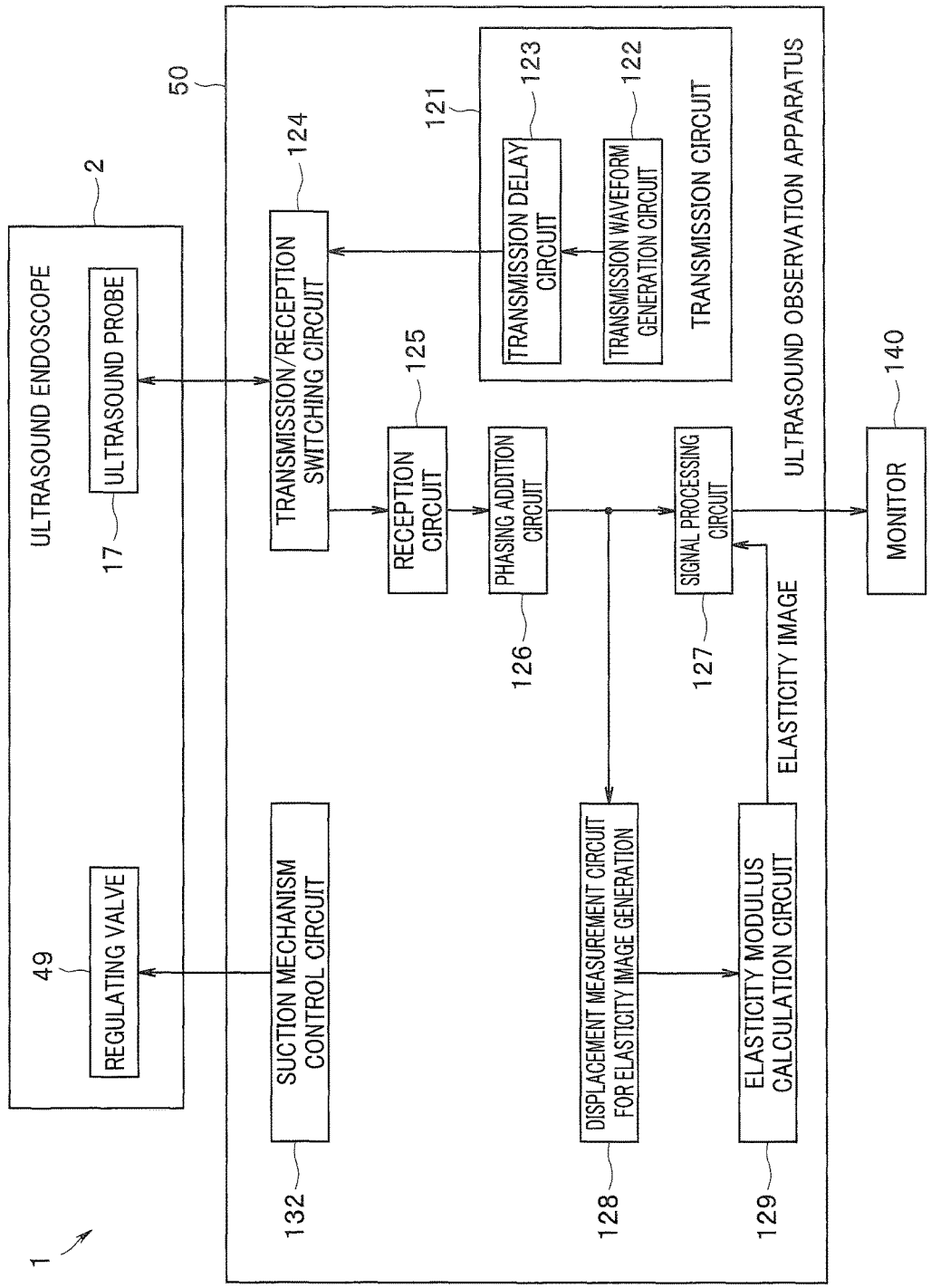
FIG. 26 is a block diagram illustrating a configuration of an ultrasound endoscope system according to a fourth embodiment of the present invention.
Figure 27:
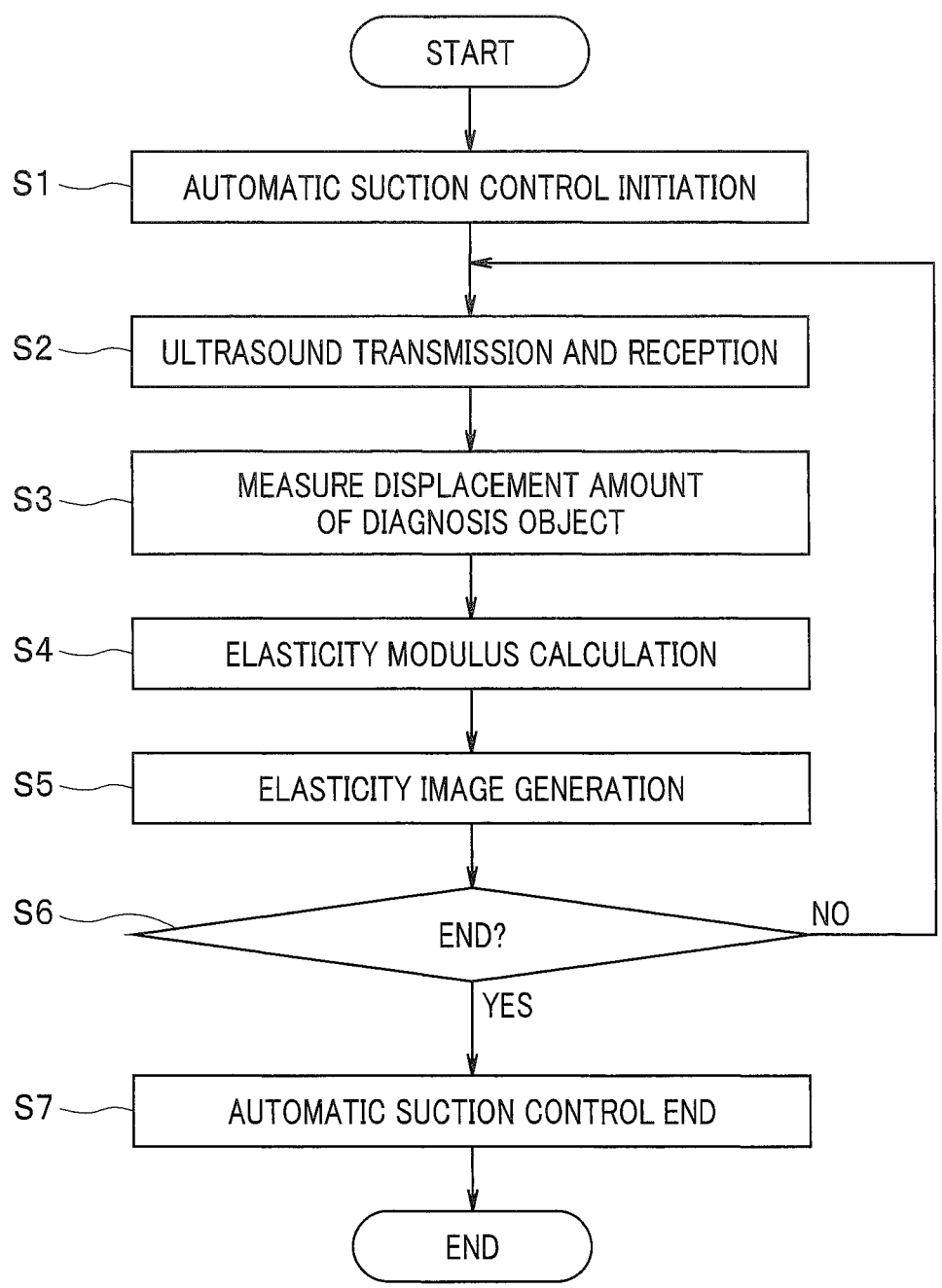
FIG. 27 is a flowchart illustrating an elasticity image generation processing routine according to the fourth embodiment of the present invention.

Next, FIGS. 26 and 27 relate to a fourth embodiment of the present invention. FIG. 26 is a block diagram illustrating the configuration of an ultrasound endoscope system. FIG. 27 is a flowchart illustrating an elasticity image generation processing routine. Note that, the present embodiment describes in detail a specific control example for a case of performing an elastography observation that is performed in the above described first embodiment. Therefore, components that are the same as in the above described first embodiment are denoted by the same reference numerals and a description thereof is omitted as appropriate. Note that, although a specific description is omitted, naturally similar control can also be applied to the above described second and third embodiments.

The ultrasound observation apparatus 50 includes a transmission circuit 121, a transmission/reception switching circuit 124, a reception circuit 125, a phasing addition circuit 126, a signal processing circuit 127, a displacement measurement circuit for elasticity image generation 128, an elasticity modulus calculation circuit 129, and a suction mechanism control circuit 132.

The transmission circuit 121 includes a transmission waveform generation circuit 122 and a transmission delay circuit 123.

The transmission waveform generation circuit 122 generates and outputs a signal waveform for driving each transducer 17a constituting the ultrasound probe 17.

The transmission delay circuit 123 regulates the drive timing of each transducer 17a constituting the ultrasound probe 17. By this means, the focal point and direction of an ultrasound beam transmitted from the ultrasound probe 17 is controlled, and the ultrasound can be converged at a desired position (depth).

The transmission/reception switching circuit 124, for example, includes a multiplexer that sequentially selects a plurality of transducers for performing transmission and reception of ultrasound, and transmits a driving signal from the transmission circuit 121 to the ultrasound probe 17, and also transmits an ultrasound signal (echo signal) from the ultrasound probe 17 to the reception circuit 125.

The reception circuit 125 receives the ultrasound signal from the transmission/reception switching circuit 124, and subjects the ultrasound signal to processing such as amplification or conversion to a digital signal.

Thus, in the present embodiment, the transmission circuit 121 (transmission waveform generation circuit 122 and transmission delay circuit 123), the transmission/reception switching circuit 124 and the reception circuit 125 realize a function as a probe control portion.

The phasing addition circuit 126 delays ultrasound signals to adjust the phases, and thereafter adds the phases.

In an ultrasound diagnosis mode, the signal processing circuit 127 performs coordinate conversion and interpolation processing on the ultrasound signal from the phasing addition circuit 126 to create an ultrasound image as an image for display. In addition, in an elasticity image observation mode (elastographic image observation mode), the signal processing circuit 127 creates an elasticity image from the elasticity modulus calculation circuit 129 as an image for display, or superimposes an elasticity image on an ultrasound image to create an image for display.

The displacement measurement circuit for elasticity image generation 128 is a displacement measurement portion for an elasticity image that is configured to measure a displacement amount for an image of a subject (displacement amount for generating an elasticity image of a subject) based on an ultrasound signal.

The elasticity modulus calculation circuit 129 is an elasticity modulus calculation portion configured to calculate an elasticity modulus of a subject based on the displacement amount for an image that is measured by the displacement measurement circuit for elasticity image generation 128. In order to calculate an elasticity modulus for each coordinate of the subject, the calculation result of the elasticity modulus calculation circuit 129 is an elasticity image in which the elasticity modulus is distributed on two-dimensional coordinates.

Thus, in the present embodiment, the phasing addition circuit 126, the signal processing circuit 127, the displacement measurement circuit for elasticity image generation 128 and the elasticity modulus calculation circuit 129 realize a function as an elasticity image generation portion. The suction mechanism control circuit 132 performs automatic pressurization (depressurization) control processing with respect to the subject, for example, upon an instruction to start elastography observation being issued through an operation of the button switch 33 or the like by a user or the like (that is, upon the elasticity image observation mode being selected). That is, at each predetermined cycle, the suction mechanism control circuit 132 performs control to open the regulating valve 49 at a predetermined duty ratio, and by controlling a negative pressure for suction that is transmitted to the suction and forceps port 22 through such valve opening control, indirectly changes a pressing state in which the ultrasound probe 17 presses the subject. It is desirable that performance of such control with respect to the regulating valve 49 is synchronized with spontaneous displacement, such as pulsation, of the subject. For example, in the present embodiment in which a pressing force on the subject by the ultrasound probe 17 is increased by the transmission of a negative pressure for suction, it is desirable that the regulating valve 49 is controlled so that the negative pressure for suction becomes smallest (or so that the negative pressure for suction becomes zero) at a timing at which a spontaneous displacement of the subject is the minimum spontaneous displacement.

Thus, in the present embodiment the suction mechanism control circuit 132 realizes a function as a pressing control portion.

The monitor 140 displays an image for display from the signal processing circuit 27.

Next, FIG. 27 is a flowchart illustrating an elasticity image generation processing routine.

The processing illustrated in FIG. 27 is started when the ultrasound endoscope system 1 is set to the elasticity image observation mode.

First, automatic pressurization control processing is initiated at the suction mechanism control circuit 132 (step S1).

Subsequently, transmission and reception of ultrasound to and from the ultrasound probe 17 is performed (step S2), and a displacement amount (displacement amount for an image) of the subject that is the diagnosis object is measured by the displacement measurement circuit for elasticity image generation 128 (step S3).

Next, based on the displacement amount for an image that is measured in step S3, the elasticity modulus calculation circuit 129 calculates an elasticity modulus of the subject for each coordinate of the subject (step S4).

The calculated elasticity moduli are sent to the signal processing circuit 127 together with the coordinates, and are used to generate an elasticity image for display (step S5). The elasticity image is, as necessary, further superimposed on an ultrasound image to create an image for display, and the image for display is displayed on the monitor 140.

Thereafter, it is determined whether or not to end the processing (step S6). If the processing is not to be ended yet, the operation returns to step S2 to repeat the above described processing in order to generate an elasticity image of the next frame.

In contrast, if it is determined that the processing is to be ended, the automatic pressurization control processing by the suction mechanism control circuit 132 is ended (step S7), to thereby end the elasticity image generation processing.

Figure 28:
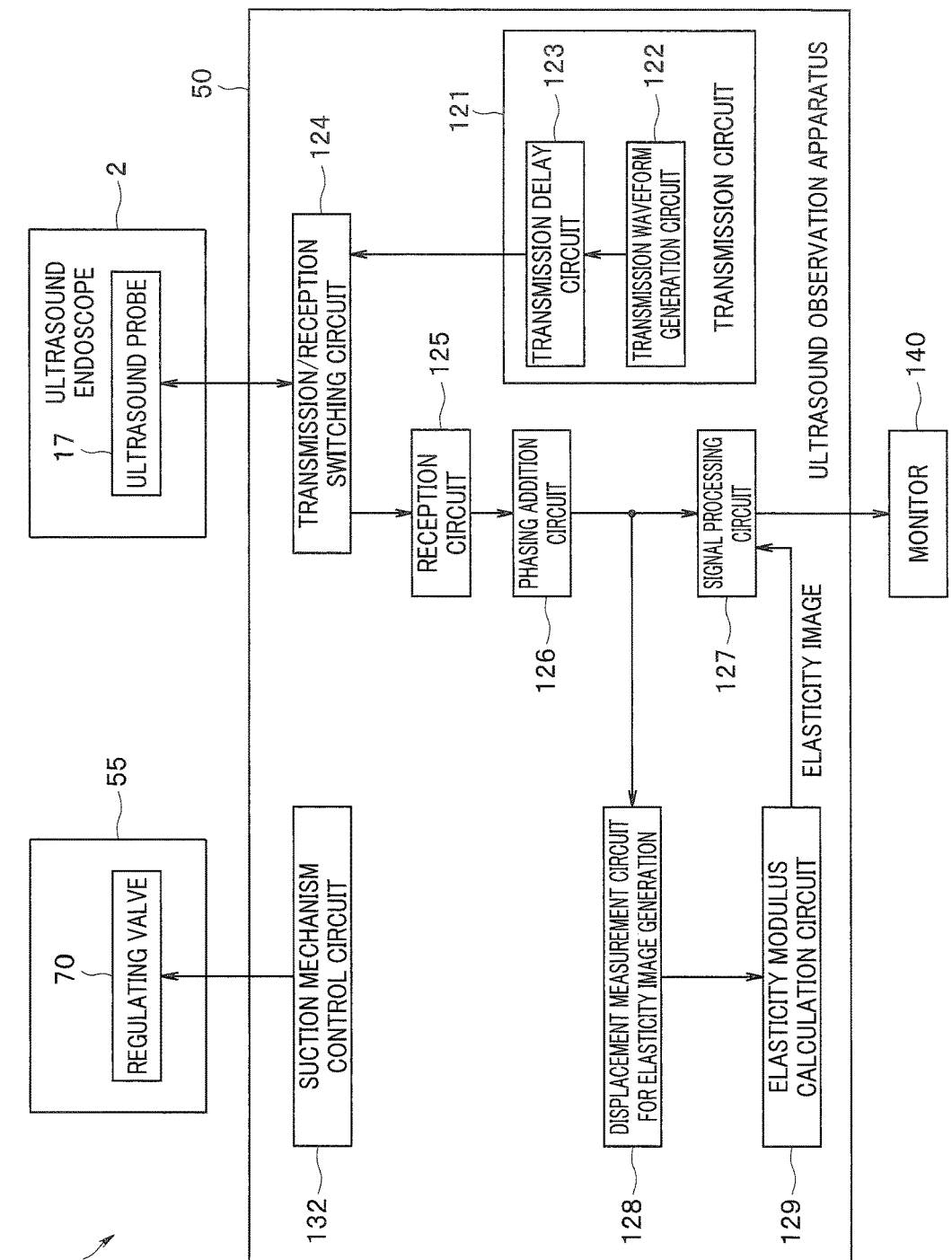
FIG. 28 is a block diagram illustrating a configuration of an ultrasound endoscope system according to a first modification of the fourth embodiment of the present invention.

Although a detailed description is omitted, for example, as shown in FIG. 28, naturally the present embodiment can be applied to the configuration described in the foregoing second embodiment.

It is to be understood that the present invention is not limited to the respective embodiments described above, and various modifications and changes are possible, and such changes and modifications are also within the technical scope of the present invention. For example, in the above described embodiments, a case of performing elastography observation by the ultrasound endoscope system 1 in order to perform an examination for tumor/lymph node metastasis or the like in the pancreas 101 is described as one example, it is also possible to apply elastography observation using the present invention to various kinds of examinations, such as examination for chronic pancreatitis, tumor/lymph node metastasis in the liver, cirrhosis of the liver, tumor/lymph node metastasis of the mediastinum (esophagus), and tumor/lymph node metastasis in the prostate gland.

Further, although in the above described embodiments an example is described of a configuration that transmits a negative pressure for suction to the vicinity of an ultrasound probe using a suction and forceps port, the present invention is not limited thereto, and naturally various modifications are possible with respect to an opening portion that transmits a negative pressure for suction as well as a negative pressure transmission path with respect to the opening portion and the like.

Naturally the configurations of the respective embodiments and respective modifications described above may also be appropriately combined.

What is claimed is:

1. An ultrasound endoscope system comprising:
    an insertion portion configured to be inserted into a subject, wherein the insertion portion comprises:
        an end face defining a suction port through which a suction force in a suction direction is controllably applied; and
        an ultrasound probe protruding in a protruding direction past the end face,
        wherein the protruding direction is different from the suction direction, and
        wherein the insertion portion defines a channel connecting the suction port to a valve and a pump, or a pump; and
    a controller configured to:
        control at least one of the valve and the pump to change a negative pressure, which is transmitted by the channel to the suction port, between at least:
            a first state which produces a first amount of the suction force to suck a targeted portion in the suction direction toward the ultrasound probe to thereby cause the ultrasound probe to press the targeted portion in the protruding direction with a first amount of pressing force; and
            a second state which produces a second amount of the suction force to suck the targeted portion in the suction direction toward the ultrasound probe to thereby cause the ultrasound probe to press the targeted portion in the protruding direction with a second amount of the pressing force;
        control the ultrasound probe to acquire a first ultrasound signal in the first state, and to acquire a second ultrasound signal in the second state; and
        generate an elastographic image representing a displacement of the targeted portion in at least the first state and the second state, based on the first ultrasound signal and the second ultrasound signal.

2. The ultrasound endoscope system according to claim 1, wherein a central axis of the suction port is positioned to intersect a scanning direction of the ultrasound probe.

3. The ultrasound endoscope system according to claim 1, wherein the controller is configured to control the at least one of the valve and the pump to periodically change the negative pressure between at least the first state and the second state.

4. The ultrasound endoscope system according to claim 3, wherein the controller is configured to control a voltage cycle of a power supply so as to control the at least one of the valve and the pump to periodically change the negative pressure between at least the first state and the second state.

5. The ultrasound endoscope system according to claim 4, wherein the controller is configured to control the at least one of the valve and the pump to periodically change the negative pressure between at least the first state and the second state synchronously with the voltage cycle.

6. The ultrasound endoscope system according to claim 1, wherein the valve is a three-way valve, and
    wherein the controller is configured to control the three-way valve so as to switch between the first state and the second state.

7. The ultrasound endoscope system according to claim 1, comprising a tubular cap configured to:
   be mounted to a distal end portion of the insertion portion so as to surround the ultrasound probe and the suction port; and
   form a negative pressure chamber between the tubular cap and the targeted portion in contact with the tubular cap as the negative pressure is applied through the suction port.

8. The ultrasound endoscope system according to claim 7, wherein the tubular cap comprises:
   a flexible tubular portion; and
   a first rigid tubular portion that is more rigid than the flexible tubular portion,
   wherein the flexible tubular portion is configured to expand and contract in an insertion direction in which the insertion portion is inserted in accordance with a change in the negative pressure inside the negative pressure chamber.

9. The ultrasound endoscope system according to claim 8, wherein the tubular cap comprises:
   a second rigid tubular portion that is more rigid than the flexible tubular portion,
   wherein the second rigid tubular portion and the first rigid tubular portion are arranged to at least partially overlap in a radial direction orthogonal to the insertion direction, and
   wherein the flexible tubular portion is provided between the first rigid tubular portion and the second rigid tubular portion.

* * * * *